US009554899B2

(12) United States Patent
Granada et al.

(10) Patent No.: US 9,554,899 B2
(45) Date of Patent: *Jan. 31, 2017

(54) SYSTEM AND METHOD FOR CARDIAC VALVE REPAIR AND REPLACEMENT

(71) Applicant: Cephea Valve Technologies, Inc., San Jose, CA (US)

(72) Inventors: Juan F. Granada, Upper Saddle River, NJ (US); Gary Erzberger, Minneapolis, MN (US); Michael P. Corcoran, Woodbury, MN (US); Dan Wallace, Santa Cruz, CA (US); Matteo Montorfano, Milan (IT); Alaide Chieffo, Milan (IT); Thierry Thaure, San Jose, CA (US)

(73) Assignee: Cephea Valve Technologies, Inc., San Jose, CA (US)

( * ) Notice: Subject to any disclaimer, the term of this patent is extended or adjusted under 35 U.S.C. 154(b) by 166 days.

This patent is subject to a terminal disclaimer.

(21) Appl. No.: 14/677,398

(22) Filed: Apr. 2, 2015

(65) Prior Publication Data

US 2015/0209139 A1    Jul. 30, 2015

Related U.S. Application Data

(63) Continuation of application No. 14/170,407, filed on Jan. 31, 2014.
(Continued)

(51) Int. Cl.
*A61F 2/24*    (2006.01)

(52) U.S. Cl.
CPC .......... *A61F 2/2412* (2013.01); *A61F 2/2409* (2013.01); *A61F 2/2418* (2013.01); *A61F 2/2436* (2013.01);
(Continued)

(58) Field of Classification Search
USPC ................................................ 623/2.11–2.18
See application file for complete search history.

(56) References Cited

U.S. PATENT DOCUMENTS 3,334,629 A    8/1967 Cohn
3,409,013 A    11/1968 Henry
(Continued)

FOREIGN PATENT DOCUMENTS

CN    1338951 A    3/2002
EP    0409929 B1    4/1997
(Continued)

OTHER PUBLICATIONS

Andersen et al.; Transluminal implantation of artificial heart valves. Description of a new expandable aortic valve and initial results with implantation by catheter technique in closed chest pigs; Euro. Heart J.; 13(5): 704-708; May 1992.
(Continued)

*Primary Examiner* — Thomas J Sweet
*Assistant Examiner* — Seema Mathew
(74) *Attorney, Agent, or Firm* — Shay Glenn LLP

(57) ABSTRACT

A prosthetic mitral valve comprising an expandable anchor comprising a first anchor, a central portion and a second anchor; wherein the first anchor comprises a first outer frame and a second outer frame, the first outer frame comprising a plurality of first arcs joined together, and the second outer frame comprising a plurality of second arcs joined together, wherein the plurality of first arcs are out of phase relative to the plurality of second arcs when the first anchor is viewed in an end view from the first anchor to the second anchor; and a plurality of replacement leaflets secured to the expandable anchor.

13 Claims, 21 Drawing Sheets

Related U.S. Application Data

(60) Provisional application No. 61/847,515, filed on Jul. 17, 2013.

(52) U.S. Cl.
CPC ...... *A61F 2/2439* (2013.01); *A61F 2230/0065* (2013.01)

(56) References Cited

U.S. PATENT DOCUMENTS

| | | |
|---|---|---|
| 3,540,431 A | 11/1970 | Mobin-Uddin |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,056,854 A | 11/1977 | Boretos et al. |
| 4,106,129 A | 8/1978 | Carpentier et al. |
| 4,233,690 A | 11/1980 | Akins |
| 4,291,420 A | 9/1981 | Reul |
| 4,326,306 A | 4/1982 | Poler |
| 4,423,809 A | 1/1984 | Mazzocco |
| 4,425,908 A | 1/1984 | Simon |
| 4,501,030 A | 2/1985 | Lane |
| 4,531,943 A | 7/1985 | Van Tassel et al. |
| 4,580,568 A | 4/1986 | Gianturco |
| 4,602,911 A | 7/1986 | Ahmadi et al. |
| 4,610,688 A | 9/1986 | Silvestrini et al. |
| 4,617,932 A | 10/1986 | Kornberg |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | DiPisa, Jr. |
| 4,665,906 A | 5/1987 | Jervis |
| 4,710,192 A | 12/1987 | Liotta et al. |
| 4,733,665 A | 3/1988 | Palmaz |
| 4,755,181 A | 7/1988 | Igoe |
| 4,796,629 A | 1/1989 | Grayzel |
| 4,819,751 A | 4/1989 | Shimada et al. |
| 4,834,755 A | 5/1989 | Silvestrini et al. |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,909,252 A | 3/1990 | Goldberger |
| 4,917,102 A | 4/1990 | Miller et al. |
| 4,927,426 A | 5/1990 | Dretler |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,064,435 A | 11/1991 | Porter |
| 5,161,547 A | 11/1992 | Tower |
| 5,163,953 A | 11/1992 | Vince |
| 5,209,741 A | 5/1993 | Spaeth |
| 5,258,042 A | 11/1993 | Mehta |
| 5,332,402 A | 7/1994 | Teitelbaum |
| 5,336,258 A | 8/1994 | Quintero et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,425,762 A | 6/1995 | Muller |
| 5,431,676 A | 7/1995 | Dubrul et al. |
| 5,443,495 A | 8/1995 | Buscemi et al. |
| 5,443,499 A | 8/1995 | Schmitt |
| 5,476,506 A | 12/1995 | Lunn |
| 5,476,510 A | 12/1995 | Eberhardt et al. |
| 5,480,423 A | 1/1996 | Ravenscroft et al. |
| 5,507,767 A | 4/1996 | Maeda et al. |
| 5,534,007 A | 7/1996 | St. Germain et al. |
| 5,545,133 A | 8/1996 | Burns et al. |
| 5,545,211 A | 8/1996 | An et al. |
| 5,549,665 A | 8/1996 | Vesely et al. |
| 5,554,185 A | 9/1996 | Block et al. |
| 5,571,215 A | 11/1996 | Sterman et al. |
| 5,573,520 A | 11/1996 | Schwartz et al. |
| 5,575,818 A | 11/1996 | Pinchuk |
| 5,645,559 A | 7/1997 | Hachtman et al. |
| 5,662,671 A | 9/1997 | Barbut et al. |
| 5,667,523 A | 9/1997 | Bynon et al. |
| 5,674,277 A | 10/1997 | Freitag |
| 5,693,083 A | 12/1997 | Baker et al. |
| 5,695,498 A | 12/1997 | Tower |
| 5,713,953 A | 2/1998 | Vallana et al. |
| 5,716,370 A | 2/1998 | Williamson et al. |
| 5,720,391 A | 2/1998 | Dohm et al. |
| 5,725,552 A * | 3/1998 | Kotula ............ A61B 17/0057 604/285 |
| 5,733,325 A | 3/1998 | Robinson et al. |
| 5,735,842 A | 4/1998 | Krueger et al. |
| 5,769,812 A | 6/1998 | Stevens et al. |
| 5,807,405 A | 9/1998 | Vanney et al. |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,843,158 A | 12/1998 | Lenker et al. |
| 5,855,597 A | 1/1999 | Jayaraman |
| 5,855,601 A | 1/1999 | Bessler et al. |
| 5,860,966 A | 1/1999 | Tower |
| 5,861,024 A | 1/1999 | Rashidi |
| 5,861,028 A | 1/1999 | Angell |
| 5,868,783 A | 2/1999 | Tower |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,907,893 A | 6/1999 | Zadno-Azizi et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,070 A | 10/1999 | Bley et al. |
| 5,984,957 A | 11/1999 | Laptewicz et al. |
| 5,984,959 A | 11/1999 | Robertson et al. |
| 5,993,469 A | 11/1999 | McKenzie et al. |
| 5,997,557 A | 12/1999 | Barbut et al. |
| 6,010,522 A | 1/2000 | Barbut et al. |
| 6,022,370 A | 2/2000 | Tower |
| 6,027,525 A | 2/2000 | Suh et al. |
| 6,042,598 A | 3/2000 | Tsugita et al. |
| 6,042,607 A | 3/2000 | Williamson et al. |
| 6,093,203 A | 7/2000 | Uflacker |
| 6,113,612 A | 9/2000 | Swanson et al. |
| 6,123,723 A | 9/2000 | Konya et al. |
| 6,142,987 A | 11/2000 | Tsugita |
| 6,162,245 A | 12/2000 | Jayaraman |
| 6,165,209 A | 12/2000 | Patterson et al. |
| 6,168,579 B1 | 1/2001 | Tsugita |
| 6,171,327 B1 | 1/2001 | Daniel et al. |
| 6,174,322 B1 | 1/2001 | Schneidt |
| 6,179,859 B1 | 1/2001 | Bates et al. |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,206,909 B1 | 3/2001 | Hanada et al. |
| 6,214,036 B1 | 4/2001 | Letendre et al. |
| 6,221,006 B1 | 4/2001 | Dubrul et al. |
| 6,221,096 B1 | 4/2001 | Aiba et al. |
| 6,231,544 B1 | 5/2001 | Tsugita et al. |
| 6,231,551 B1 | 5/2001 | Barbut |
| 6,241,757 B1 | 6/2001 | An et al. |
| 6,245,102 B1 | 6/2001 | Jayaraman |

(56) References Cited

U.S. PATENT DOCUMENTS

| | | | |
|---|---|---|---|
| 6,251,135 B1 | 6/2001 | Stinson et al. | |
| 6,258,114 B1 | 7/2001 | Konya et al. | |
| 6,258,115 B1 | 7/2001 | Dubrul | |
| 6,258,120 B1 | 7/2001 | McKenzie et al. | |
| 6,277,555 B1 | 8/2001 | Duran et al. | |
| 6,309,417 B1 | 10/2001 | Spence et al. | |
| 6,319,281 B1 | 11/2001 | Patel | |
| 6,336,934 B1 | 1/2002 | Gilson et al. | |
| 6,336,937 B1 | 1/2002 | Vonesh et al. | |
| 6,338,735 B1 | 1/2002 | Stevens | |
| 6,348,063 B1 | 2/2002 | Yassour et al. | |
| 6,352,708 B1 | 3/2002 | Duran et al. | |
| 6,361,545 B1 | 3/2002 | Macoviak et al. | |
| 6,371,970 B1 | 4/2002 | Khosravi et al. | |
| 6,371,983 B1 | 4/2002 | Lane | |
| 6,379,368 B1 | 4/2002 | Corcoran et al. | |
| 6,379,383 B1 | 4/2002 | Palmaz et al. | |
| 6,398,807 B1 | 6/2002 | Chouinard et al. | |
| 6,409,750 B1 | 6/2002 | Hyodoh et al. | |
| 6,411,552 B1 | 6/2002 | Chiba | |
| 6,416,510 B1 | 7/2002 | Altman et al. | |
| 6,419,696 B1 | 7/2002 | Ortiz et al. | |
| 6,425,916 B1 | 7/2002 | Garrison et al. | |
| 6,440,152 B1 * | 8/2002 | Gainor | A61B 17/0057 606/213 |
| 6,440,164 B1 | 8/2002 | DiMatteo et al. | |
| 6,454,799 B1 | 9/2002 | Schreck | |
| 6,458,153 B1 | 10/2002 | Bailey et al. | |
| 6,468,303 B1 * | 10/2002 | Amplatz | A61B 17/11 623/1.2 |
| 6,475,239 B1 | 11/2002 | Campbell et al. | |
| 6,482,228 B1 | 11/2002 | Norred | |
| 6,485,502 B2 | 11/2002 | Don Michael et al. | |
| 6,494,909 B2 | 12/2002 | Greenhalgh | |
| 6,503,272 B2 | 1/2003 | Duerig et al. | |
| 6,527,800 B1 | 3/2003 | McGuckin et al. | |
| 6,540,768 B1 | 4/2003 | Diaz et al. | |
| 6,562,058 B2 | 5/2003 | Seguin et al. | |
| 6,592,546 B1 | 7/2003 | Barbut et al. | |
| 6,592,614 B2 | 7/2003 | Lenker et al. | |
| 6,610,077 B1 | 8/2003 | Hancock et al. | |
| 6,616,675 B1 | 9/2003 | Evard et al. | |
| 6,616,682 B2 | 9/2003 | Joergensen et al. | |
| 6,622,604 B1 | 9/2003 | Chouinard et al. | |
| 6,623,518 B2 | 9/2003 | Thompson et al. | |
| 6,635,068 B1 | 10/2003 | Dubrul et al. | |
| 6,635,079 B2 | 10/2003 | Unsworth et al. | |
| 6,652,571 B1 | 11/2003 | White et al. | |
| 6,656,206 B2 | 12/2003 | Corcoran et al. | |
| 6,663,588 B2 | 12/2003 | DuBois et al. | |
| 6,663,663 B2 | 12/2003 | Kim et al. | |
| 6,669,724 B2 | 12/2003 | Park et al. | |
| 6,673,089 B1 | 1/2004 | Yassour et al. | |
| 6,673,109 B2 | 1/2004 | Cox | |
| 6,676,668 B2 | 1/2004 | Mercereau et al. | |
| 6,676,692 B2 | 1/2004 | Rabkin et al. | |
| 6,676,698 B2 | 1/2004 | McGuckin et al. | |
| 6,682,558 B2 | 1/2004 | Tu et al. | |
| 6,682,559 B2 | 1/2004 | Myers et al. | |
| 6,689,144 B2 | 2/2004 | Gerberding | |
| 6,689,164 B1 | 2/2004 | Seguin | |
| 6,692,512 B2 | 2/2004 | Jang | |
| 6,695,864 B2 | 2/2004 | Macoviak et al. | |
| 6,695,865 B2 | 2/2004 | Boyle et al. | |
| 6,702,851 B1 | 3/2004 | Chinn et al. | |
| 6,712,836 B1 * | 3/2004 | Berg | A61B 17/0057 606/213 |
| 6,712,842 B1 | 3/2004 | Gifford et al. | |
| 6,712,843 B2 | 3/2004 | Elliott | |
| 6,714,842 B1 | 3/2004 | Ito | |
| 6,723,122 B2 | 4/2004 | Yang et al. | |
| 6,730,118 B2 | 5/2004 | Spenser et al. | |
| 6,730,377 B2 | 5/2004 | Wang | |
| 6,733,525 B2 | 5/2004 | Pease et al. | |
| 6,752,828 B2 | 6/2004 | Thornton | |
| 6,758,855 B2 | 7/2004 | Fulton et al. | |
| 6,764,503 B1 | 7/2004 | Ishimaru | |
| 6,764,509 B2 | 7/2004 | Chinn et al. | |
| 6,767,345 B2 | 7/2004 | St. Germain et al. | |
| 6,773,454 B2 | 8/2004 | Wholey et al. | |
| 6,776,791 B1 | 8/2004 | Stallings et al. | |
| 6,790,218 B2 * | 9/2004 | Jayaraman | 606/191 |
| 6,790,229 B1 | 9/2004 | Berreklouw | |
| 6,790,230 B2 | 9/2004 | Beyersdorf et al. | |
| 6,790,237 B2 | 9/2004 | Stinson | |
| 6,792,979 B2 | 9/2004 | Konya et al. | |
| 6,814,746 B2 | 11/2004 | Thompson et al. | |
| 6,821,297 B2 | 11/2004 | Snyders | |
| 6,837,901 B2 | 1/2005 | Rabkin et al. | |
| 6,843,802 B1 | 1/2005 | Villalobos et al. | |
| 6,849,085 B2 | 2/2005 | Marton | |
| 6,863,668 B2 | 3/2005 | Gillespie et al. | |
| 6,872,223 B2 | 3/2005 | Roberts et al. | |
| 6,872,226 B2 | 3/2005 | Cali et al. | |
| 6,875,231 B2 | 4/2005 | Anduiza et al. | |
| 6,881,220 B2 | 4/2005 | Edwin et al. | |
| 6,887,266 B2 | 5/2005 | Williams et al. | |
| 6,890,340 B2 | 5/2005 | Duane | |
| 6,893,459 B1 | 5/2005 | Macoviak | |
| 6,893,460 B2 | 5/2005 | Spenser et al. | |
| 6,905,743 B1 | 6/2005 | Chen et al. | |
| 6,908,481 B2 | 6/2005 | Cribier | |
| 6,911,036 B2 | 6/2005 | Douk et al. | |
| 6,911,037 B2 * | 6/2005 | Gainor | A61B 17/0057 606/213 |
| 6,913,614 B2 * | 7/2005 | Marino | A61B 17/0057 606/213 |
| 6,921,397 B2 | 7/2005 | Corcoran et al. | |
| 6,936,058 B2 | 8/2005 | Forde et al. | |
| 6,936,067 B2 | 8/2005 | Buchanan | |
| 6,953,332 B1 | 10/2005 | Kurk et al. | |
| 6,960,220 B2 | 11/2005 | Marino et al. | |
| 6,960,224 B2 | 11/2005 | Marino et al. | |
| 6,974,464 B2 | 12/2005 | Quijano et al. | |
| 6,974,476 B2 | 12/2005 | McGuckin et al. | |
| 6,979,350 B2 | 12/2005 | Moll et al. | |
| 6,984,242 B2 | 1/2006 | Campbell et al. | |
| 7,011,681 B2 | 3/2006 | Vesely | |
| 7,018,406 B2 | 3/2006 | Seguin et al. | |
| 7,025,791 B2 | 4/2006 | Levine et al. | |
| 7,037,331 B2 | 5/2006 | Mitelberg et al. | |
| 7,077,861 B2 | 7/2006 | Spence | |
| 7,087,072 B2 | 8/2006 | Marino et al. | |
| 7,115,135 B2 | 10/2006 | Corcoran et al. | |
| 7,122,020 B2 | 10/2006 | Mogul | |
| 7,144,410 B2 | 12/2006 | Marino et al. | |
| 7,166,097 B2 | 1/2007 | Barbut | |
| 7,175,653 B2 | 2/2007 | Gaber | |
| 7,175,654 B2 | 2/2007 | Bonsignore et al. | |
| 7,189,258 B2 | 3/2007 | Johnson et al. | |
| 7,191,018 B2 | 3/2007 | Gielen et al. | |
| 7,192,435 B2 | 3/2007 | Corcoran et al. | |
| 7,201,772 B2 | 4/2007 | Schwammenthal et al. | |
| 7,235,093 B2 | 6/2007 | Gregorich | |
| 7,320,704 B2 | 1/2008 | Lashinski et al. | |
| 7,329,279 B2 | 2/2008 | Haug et al. | |
| 7,374,560 B2 | 5/2008 | Ressemann et al. | |
| 7,381,219 B2 | 6/2008 | Salahieh et al. | |
| 7,413,563 B2 | 8/2008 | Corcoran et al. | |
| 7,445,631 B2 | 11/2008 | Salahieh et al. | |
| 7,566,336 B2 | 7/2009 | Corcoran et al. | |
| 7,582,104 B2 | 9/2009 | Corcoran et al. | |
| 7,591,848 B2 | 9/2009 | Allen | |
| 7,625,364 B2 | 12/2009 | Corcoran et al. | |
| 7,632,298 B2 | 12/2009 | Hijlkema et al. | |
| 7,658,748 B2 | 2/2010 | Marino et al. | |
| 7,691,115 B2 | 4/2010 | Corcoran et al. | |
| 7,712,606 B2 | 5/2010 | Salahieh et al. | |
| 7,722,666 B2 | 5/2010 | LaFontaine | |
| 7,748,389 B2 | 7/2010 | Salahieh et al. | |
| 7,749,238 B2 | 7/2010 | Corcoran et al. | |
| 7,780,725 B2 | 8/2010 | Haug et al. | |
| 7,803,184 B2 | 9/2010 | McGuckin et al. | |
| 7,824,442 B2 | 11/2010 | Salahieh et al. | |

(56) References Cited

U.S. PATENT DOCUMENTS

| | | | |
|---|---|---|---|
| 7,824,443 B2 | 11/2010 | Salahieh et al. | |
| 7,896,915 B2 * | 3/2011 | Guyenot | A61F 2/2418 623/1.24 |
| 7,905,901 B2 | 3/2011 | Corcoran et al. | |
| 7,927,351 B2 | 4/2011 | Corcoran et al. | |
| 7,972,361 B2 | 7/2011 | Corcoran et al. | |
| 8,043,368 B2 | 10/2011 | Crabtree | |
| 8,092,520 B2 | 1/2012 | Quadri | |
| 8,167,935 B2 | 5/2012 | McGuckin et al. | |
| 8,236,049 B2 * | 8/2012 | Rowe | A61F 2/2418 623/2.11 |
| 8,317,858 B2 * | 11/2012 | Straubinger | A61F 2/2418 623/1.15 |
| 8,366,741 B2 | 2/2013 | Chin et al. | |
| 8,398,708 B2 * | 3/2013 | Meiri | A61B 17/0487 623/2.11 |
| 8,444,689 B2 * | 5/2013 | Zhang | A61F 2/2418 623/2.1 |
| 8,449,599 B2 | 5/2013 | Chau et al. | |
| 8,551,132 B2 * | 10/2013 | Eskridge | A61B 17/12022 606/191 |
| 8,551,161 B2 | 10/2013 | Dolan | |
| 8,579,964 B2 | 11/2013 | Lane et al. | |
| 8,579,966 B2 | 11/2013 | Seguin et al. | |
| 8,623,074 B2 | 1/2014 | Ryan | |
| 8,685,080 B2 | 4/2014 | White | |
| 8,728,155 B2 | 5/2014 | Montorfano et al. | |
| 8,740,962 B2 * | 6/2014 | Finch | A61B 17/0057 623/1.11 |
| 8,795,356 B2 | 8/2014 | Quadri et al. | |
| 8,852,272 B2 * | 10/2014 | Gross | A61F 2/2436 623/1.26 |
| 8,870,948 B1 | 10/2014 | Erzberger et al. | |
| 8,894,702 B2 | 11/2014 | Quadri et al. | |
| 8,911,455 B2 | 12/2014 | Quadri et al. | |
| 9,017,399 B2 * | 4/2015 | Gross | A61B 17/068 623/2.1 |
| 9,023,074 B2 * | 5/2015 | Theobald | A61B 17/0057 606/191 |
| 9,023,100 B2 | 5/2015 | Quadri et al. | |
| 9,034,032 B2 * | 5/2015 | McLean | A61F 2/2436 623/2.12 |
| 9,039,757 B2 * | 5/2015 | McLean | A61F 2/2436 623/1.24 |
| 2001/0007956 A1 | 7/2001 | Letac et al. | |
| 2001/0039450 A1 | 11/2001 | Pavcnik et al. | |
| 2001/0041928 A1 | 11/2001 | Pavcnik et al. | |
| 2001/0041930 A1 | 11/2001 | Globerman et al. | |
| 2001/0044652 A1 | 11/2001 | Moore | |
| 2001/0044656 A1 | 11/2001 | Williamson et al. | |
| 2002/0002396 A1 | 1/2002 | Fulkerson | |
| 2002/0010489 A1 | 1/2002 | Grayzel et al. | |
| 2002/0026233 A1 | 2/2002 | Shaknovich | |
| 2002/0029981 A1 | 3/2002 | Nigam | |
| 2002/0032481 A1 | 3/2002 | Gabbay | |
| 2002/0055769 A1 | 5/2002 | Wang | |
| 2002/0062135 A1 * | 5/2002 | Mazzocchi | A61B 17/12022 606/200 |
| 2002/0082609 A1 | 6/2002 | Green | |
| 2002/0095173 A1 | 7/2002 | Mazzocchi et al. | |
| 2002/0120328 A1 | 8/2002 | Pathak et al. | |
| 2002/0161392 A1 | 10/2002 | Dubrul | |
| 2002/0161394 A1 | 10/2002 | Macoviak et al. | |
| 2002/0177766 A1 | 11/2002 | Mogul | |
| 2002/0183781 A1 | 12/2002 | Casey et al. | |
| 2002/0188341 A1 | 12/2002 | Elliott | |
| 2002/0188344 A1 | 12/2002 | Bolea et al. | |
| 2003/0023303 A1 | 1/2003 | Palmaz et al. | |
| 2003/0036791 A1 | 2/2003 | Philipp et al. | |
| 2003/0040771 A1 | 2/2003 | Hyodoh et al. | |
| 2003/0040772 A1 | 2/2003 | Hyodoh et al. | |
| 2003/0040791 A1 | 2/2003 | Oktay | |
| 2003/0050694 A1 | 3/2003 | Yang et al. | |
| 2003/0055495 A1 | 3/2003 | Pease et al. | |
| 2003/0060844 A1 | 3/2003 | Borillo et al. | |
| 2003/0070944 A1 | 4/2003 | Nigam | |
| 2003/0109924 A1 | 6/2003 | Cribier | |
| 2003/0109930 A1 | 6/2003 | Bluni et al. | |
| 2003/0114912 A1 | 6/2003 | Sequin et al. | |
| 2003/0130729 A1 | 7/2003 | Paniagua et al. | |
| 2003/0135257 A1 | 7/2003 | Taheri | |
| 2003/0144732 A1 | 7/2003 | Cosgrove et al. | |
| 2003/0149476 A1 | 8/2003 | Damm et al. | |
| 2003/0149478 A1 * | 8/2003 | Figulla | A61F 2/2418 623/2.38 |
| 2003/0176884 A1 | 9/2003 | Berrada et al. | |
| 2003/0181850 A1 | 9/2003 | Diamond et al. | |
| 2003/0187495 A1 | 10/2003 | Cully et al. | |
| 2003/0199971 A1 | 10/2003 | Tower et al. | |
| 2003/0208224 A1 | 11/2003 | Broome | |
| 2003/0212429 A1 | 11/2003 | Keegan et al. | |
| 2003/0212454 A1 | 11/2003 | Scott et al. | |
| 2003/0216774 A1 | 11/2003 | Larson | |
| 2003/0225421 A1 * | 12/2003 | Peavey | A61B 17/0057 606/151 |
| 2003/0225445 A1 | 12/2003 | Derus et al. | |
| 2003/0229390 A1 | 12/2003 | Ashton et al. | |
| 2003/0233117 A1 | 12/2003 | Adams et al. | |
| 2004/0034411 A1 | 2/2004 | Quijano et al. | |
| 2004/0049226 A1 | 3/2004 | Buehlmann et al. | |
| 2004/0049262 A1 | 3/2004 | Keegan et al. | |
| 2004/0049262 A1 | 3/2004 | Obermiller et al. | |
| 2004/0060563 A1 | 4/2004 | Rapacki et al. | |
| 2004/0082904 A1 | 4/2004 | Houde et al. | |
| 2004/0082967 A1 | 4/2004 | Broome et al. | |
| 2004/0087982 A1 | 5/2004 | Eskuri | |
| 2004/0093016 A1 | 5/2004 | Root et al. | |
| 2004/0098022 A1 | 5/2004 | Barone | |
| 2004/0098099 A1 | 5/2004 | McCullagh et al. | |
| 2004/0111096 A1 | 6/2004 | Tu et al. | |
| 2004/0116951 A1 | 6/2004 | Rosengart | |
| 2004/0117004 A1 | 6/2004 | Osborne et al. | |
| 2004/0122468 A1 | 6/2004 | Yodfat et al. | |
| 2004/0127936 A1 | 7/2004 | Salahieh et al. | |
| 2004/0127979 A1 | 7/2004 | Wilson et al. | |
| 2004/0133274 A1 | 7/2004 | Webler et al. | |
| 2004/0138694 A1 | 7/2004 | Tran et al. | |
| 2004/0143294 A1 * | 7/2004 | Corcoran | A61B 17/0057 606/213 |
| 2004/0148021 A1 | 7/2004 | Cartledge et al. | |
| 2004/0153094 A1 | 8/2004 | Dunfee et al. | |
| 2004/0158277 A1 | 8/2004 | Lowe et al. | |
| 2004/0167565 A1 | 8/2004 | Beulke et al. | |
| 2004/0181140 A1 | 9/2004 | Falwell et al. | |
| 2004/0186563 A1 | 9/2004 | Lobbi | |
| 2004/0204755 A1 | 10/2004 | Robin | |
| 2004/0215331 A1 | 10/2004 | Chew et al. | |
| 2004/0215339 A1 | 10/2004 | Drasler et al. | |
| 2004/0220655 A1 | 11/2004 | Swanson et al. | |
| 2004/0225321 A1 | 11/2004 | Krolik et al. | |
| 2004/0254636 A1 | 12/2004 | Flagle et al. | |
| 2005/0033402 A1 | 2/2005 | Cully et al. | |
| 2005/0065548 A1 * | 3/2005 | Marino | A61B 17/0057 606/213 |
| 2005/0070934 A1 * | 3/2005 | Tanaka | A61B 17/1114 606/153 |
| 2005/0075662 A1 | 4/2005 | Pedersen et al. | |
| 2005/0085841 A1 | 4/2005 | Eversull et al. | |
| 2005/0085842 A1 | 4/2005 | Eversull et al. | |
| 2005/0085843 A1 | 4/2005 | Opolski et al. | |
| 2005/0085890 A1 | 4/2005 | Rasmussen et al. | |
| 2005/0090846 A1 | 4/2005 | Pedersen et al. | |
| 2005/0096692 A1 | 5/2005 | Linder et al. | |
| 2005/0096734 A1 | 5/2005 | Majercak et al. | |
| 2005/0096735 A1 | 5/2005 | Hojeibane et al. | |
| 2005/0096736 A1 | 5/2005 | Osse et al. | |
| 2005/0096738 A1 | 5/2005 | Cali et al. | |
| 2005/0100580 A1 | 5/2005 | Osborne et al. | |
| 2005/0107822 A1 | 5/2005 | WasDyke | |
| 2005/0113910 A1 | 5/2005 | Paniagua et al. | |
| 2005/0137686 A1 | 6/2005 | Salahieh et al. | |
| 2005/0137687 A1 | 6/2005 | Salahieh et al. | |
| 2005/0137688 A1 | 6/2005 | Salahieh et al. | |

(56) References Cited

U.S. PATENT DOCUMENTS

| | | |
|---|---|---|
| 2005/0137689 A1 | 6/2005 | Salahieh et al. |
| 2005/0137690 A1* | 6/2005 | Salahieh ............... A61F 2/2418 623/2.11 |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137696 A1 | 6/2005 | Salahieh et al. |
| 2005/0137697 A1 | 6/2005 | Salahieh et al. |
| 2005/0137701 A1 | 6/2005 | Salahieh et al. |
| 2005/0143809 A1 | 6/2005 | Salahieh et al. |
| 2005/0165352 A1 | 7/2005 | Henry et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0209580 A1 | 9/2005 | Freyman |
| 2005/0228472 A1 | 10/2005 | Case et al. |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283962 A1* | 12/2005 | Boudjemline ..... A61B 17/0057 29/433 |
| 2005/0288766 A1 | 12/2005 | Plain et al. |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0058872 A1 | 3/2006 | Salahieh et al. |
| 2006/0116717 A1 | 6/2006 | Marino et al. |
| 2006/0155312 A1 | 7/2006 | Levine et al. |
| 2006/0161249 A1 | 7/2006 | Realyvasquez et al. |
| 2006/0195183 A1 | 8/2006 | Navia et al. |
| 2006/0235510 A1 | 10/2006 | Johnson et al. |
| 2006/0247680 A1* | 11/2006 | Amplatz ............ A61B 17/0057 606/213 |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0271166 A1 | 11/2006 | Thill et al. |
| 2006/0287668 A1 | 12/2006 | Fawzi et al. |
| 2007/0016286 A1 | 1/2007 | Herrmann et al. |
| 2007/0055340 A1 | 3/2007 | Pryor |
| 2007/0088431 A1 | 4/2007 | Bourang et al. |
| 2007/0100440 A1 | 5/2007 | Figulla et al. |
| 2007/0112355 A1 | 5/2007 | Salahieh et al. |
| 2007/0118214 A1 | 5/2007 | Salahieh et al. |
| 2007/0203503 A1 | 8/2007 | Salahieh et al. |
| 2007/0244552 A1 | 10/2007 | Salahieh et al. |
| 2007/0265656 A1* | 11/2007 | Amplatz ............ A61B 17/0057 606/200 |
| 2007/0276324 A1 | 11/2007 | Laduca et al. |
| 2007/0288089 A1 | 12/2007 | Gurskis et al. |
| 2008/0015619 A1* | 1/2008 | Figulla ............... A61B 17/0057 606/157 |
| 2008/0033543 A1 | 2/2008 | Gurskis et al. |
| 2008/0082165 A1 | 4/2008 | Wilson et al. |
| 2008/0140189 A1 | 6/2008 | Nguyen et al. |
| 2008/0167682 A1* | 7/2008 | Corcoran ........... A61B 17/0057 606/215 |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0288054 A1 | 11/2008 | Pulnev et al. |
| 2009/0005863 A1 | 1/2009 | Goetz et al. |
| 2009/0062841 A1* | 3/2009 | Amplatz ............. A61B 17/0057 606/200 |
| 2009/0082803 A1* | 3/2009 | Adams ............... A61B 17/0057 606/213 |
| 2009/0171456 A1 | 7/2009 | Kveen et al. |
| 2009/0182405 A1 | 7/2009 | De La Menardiere et al. |
| 2009/0192585 A1 | 7/2009 | Bloom et al. |
| 2009/0222076 A1 | 9/2009 | Figulla et al. |
| 2009/0254165 A1 | 10/2009 | Tabor et al. |
| 2009/0264759 A1 | 10/2009 | Byrd |
| 2009/0287290 A1 | 11/2009 | Macaulay et al. |
| 2010/0049313 A1 | 2/2010 | Alon et al. |
| 2010/0082094 A1* | 4/2010 | Quadri ................ A61F 2/2412 623/1.26 |
| 2010/0121434 A1 | 5/2010 | Paul et al. |
| 2010/0219092 A1 | 9/2010 | Salahieh et al. |
| 2010/0280495 A1 | 11/2010 | Paul et al. |
| 2010/0284724 A1 | 11/2010 | Cardia |
| 2010/0312333 A1 | 12/2010 | Navia et al. |
| 2011/0004296 A1* | 1/2011 | Lutter ................ A61B 17/0401 623/1.26 |
| 2011/0137397 A1* | 6/2011 | Chau .................. A61F 2/2418 623/1.11 |
| 2011/0218619 A1* | 9/2011 | Benichou ............ A61F 2/2412 623/2.11 |
| 2011/0245911 A1 | 10/2011 | Quill et al. |
| 2011/0257723 A1* | 10/2011 | Mcnamara ......... A61B 17/0057 623/1.11 |
| 2011/0264198 A1 | 10/2011 | Murray et al. |
| 2011/0295363 A1 | 12/2011 | Girard et al. |
| 2011/0301702 A1* | 12/2011 | Rust .................. A61F 2/2418 623/2.11 |
| 2012/0059458 A1* | 3/2012 | Buchbinder .......... A61F 2/2409 623/2.36 |
| 2013/0041447 A1 | 2/2013 | Erb et al. |
| 2013/0041458 A1 | 2/2013 | Lashinski et al. |
| 2013/0253643 A1* | 9/2013 | Rolando .............. A61F 2/2445 623/2.37 |
| 2013/0261737 A1* | 10/2013 | Costello ............. A61F 2/2418 623/2.11 |
| 2013/0282110 A1 | 10/2013 | Schweich, Jr. et al. |
| 2013/0282114 A1 | 10/2013 | Schweich, Jr. et al. |
| 2013/0304197 A1* | 11/2013 | Buchbinder .......... A61F 2/2427 623/2.11 |
| 2013/0304200 A1* | 11/2013 | McLean ............. A61F 2/2436 623/2.18 |
| 2013/0310923 A1 | 11/2013 | Kheradvar et al. |
| 2013/0331931 A1 | 12/2013 | Gregg et al. |
| 2014/0005778 A1* | 1/2014 | Buchbinder et al. ........ 623/2.18 |
| 2014/0012368 A1* | 1/2014 | Sugimoto ............ A61L 31/022 623/2.11 |
| 2014/0052237 A1* | 2/2014 | Lane .................. A61F 2/2412 623/2.11 |
| 2014/0052244 A1* | 2/2014 | Rolando .............. A61F 2/2409 623/2.37 |
| 2014/0214159 A1* | 7/2014 | Vidlund .................. A61L 27/34 623/2.14 |
| 2014/0222136 A1* | 8/2014 | Geist .................. A61F 2/2466 623/2.11 |
| 2014/0243954 A1* | 8/2014 | Shannon .................... A61F 2/24 623/2.11 |
| 2014/0249622 A1* | 9/2014 | Carmi ................. A61F 2/2442 623/2.11 |
| 2014/0257476 A1 | 9/2014 | Montorfano et al. |
| 2014/0324164 A1 | 10/2014 | Gross et al. |
| 2015/0025623 A1 | 1/2015 | Granada et al. |
| 2015/0135506 A1 | 5/2015 | White |
| 2015/0157457 A1* | 6/2015 | Hacohen ............ A61B 17/0401 623/2.11 |
| 2015/0164640 A1* | 6/2015 | McLean ............. A61F 2/2436 623/2.37 |
| 2015/0173897 A1 | 6/2015 | Raanani et al. |

FOREIGN PATENT DOCUMENTS

| | | |
|---|---|---|
| EP | 1057459 A1 | 12/2000 |
| EP | 1057460 A1 | 12/2000 |
| EP | 0937439 B1 | 9/2003 |
| EP | 1340473 A2 | 9/2003 |
| EP | 1356793 A2 | 10/2003 |
| EP | 1042045 B1 | 5/2004 |
| EP | 0819013 B1 | 6/2004 |
| EP | 1229864 B1 | 4/2005 |

(56) References Cited

FOREIGN PATENT DOCUMENTS

| | | |
|---|---|---|
| EP | 1430853 A2 | 6/2005 |
| EP | 1059894 B1 | 7/2005 |
| EP | 1078610 B1 | 8/2005 |
| EP | 1469797 B1 | 11/2005 |
| EP | 1600121 A1 | 11/2005 |
| EP | 1616531 A2 | 1/2006 |
| EP | 1849440 A1 | 10/2007 |
| WO | WO95/04556 A2 | 2/1995 |
| WO | WO95/29640 A1 | 11/1995 |
| WO | WO96/14032 A1 | 5/1996 |
| WO | WO96/24306 A1 | 8/1996 |
| WO | WO98/36790 A1 | 8/1998 |
| WO | WO98/57599 A2 | 12/1998 |
| WO | WO99/44542 A2 | 9/1999 |
| WO | WO00/09059 A2 | 2/2000 |
| WO | WO00/44308 A2 | 8/2000 |
| WO | WO00/44313 A1 | 8/2000 |
| WO | WO00/67661 A2 | 11/2000 |
| WO | WO01/05331 A1 | 1/2001 |
| WO | WO01/35870 A1 | 5/2001 |
| WO | WO01/64137 A1 | 9/2001 |
| WO | WO02/36048 A1 | 5/2002 |
| WO | WO02/41789 A2 | 5/2002 |
| WO | WO02/100297 A2 | 12/2002 |
| WO | WO03/003943 A2 | 1/2003 |
| WO | WO03/003949 A2 | 1/2003 |
| WO | WO03/011195 A2 | 2/2003 |
| WO | WO03/030776 A2 | 4/2003 |
| WO | WO03/015851 A1 | 11/2003 |
| WO | WO03/094797 A1 | 11/2003 |
| WO | WO2004/014256 A1 | 2/2004 |
| WO | WO2004/019811 A2 | 3/2004 |
| WO | WO2004/026117 A2 | 4/2004 |
| WO | WO2004/041126 A1 | 5/2004 |
| WO | WO2004/047681 A1 | 6/2004 |
| WO | WO2004/066876 A1 | 8/2004 |
| WO | WO2004/082536 A1 | 9/2004 |
| WO | WO2005/084595 A1 | 9/2005 |
| WO | WO2005/087140 A1 | 9/2005 |
| WO | WO2009/072122 A1 | 6/2009 |
| WO | WO2009/108615 A1 | 9/2009 |
| WO | WO2009/132187 A1 | 10/2009 |
| WO | WO2009/137755 A2 | 11/2009 |
| WO | WO2013/158608 A1 | 10/2013 |
| WO | WO2013/158613 A1 | 10/2013 |

OTHER PUBLICATIONS

Atwood et al.; Insertion of Heart Valves by Catheterization; Project Supervised by Prof. S. Muftu of Northeastern University, May 2002: pp. 36-40.
Bodnar et al. Replacement Cardiac Valves R Chapter 13: Extinct cardiac valve prostheses. Pergamon Publishing Corporation. New York, 1991: 307-322 (year of pub. sufficiently earlier than effective US filing date and any foreign priority date).
Boudjemline et al. Percutaneous implantation of a biological valve in the aorta to treat aortic valve insufficiency—a sheep study.f Med Sci. Monit; Apr. 2002; vol. 8, No. 4: BR113-116.
Boudjemline et al. "Percutaneous implantation of a valve in the descending aorta in lambs." Euro. Heart J; Jul. 2002; 23: 1045-1049.
Boudjemline et al. "Percutaneous pulmonary valve replacement in a large right ventricular outflow tract: an experimental study." Journal of the Americal College of Cardiology; Mar. 2004; vol. 43(6): 1082-1087.
Boudjemline et al. "Percutaneous valve insertion: A new approach?" J. of Thoracic and Cardio. Surg; Mar. 2003; 125(3): 741-743.

Boudjemline et al. "Steps Toward Percutaneous Aortic Valve Replacement." Circulation; Feb. 2002; 105: 775-778.
Cribier et al. "Early Experience with Percutaneous Transcatheter Implantation of Heart Valve Prosthesis for the Treatment of End-Stage Inoperable Patients with Calcific Aortic Stenosis." J. of Am. Coll. of Cardio; Feb. 2004; 43(4): 698-703.
Cribier et al. "Percutaneous Transcatheter Implantation of an Aortic Valve Prosthesis for Calcific Aortic Stenosis: First Human Case Description." Circulation; Dec. 2002; 106: 3006-3008.
Cribier et al. "Percutaneous Transcatheter Implantation of an Aortic Valve Prosthesis for Calcific Aortic Stenosis: First Human Case." Percutaneous Valve Technologies, Inc. 2002: 16 pages (year of pub. sufficiently earlier than effective US filed and any foreign priority date).
Ferrari et al. "Percutaneous transvascular aortic valve replacement with self expanding stent-valve device." Poster from the presentation given at SMIT 2000, 12th International Conference. 1 pg. Sep. 5, 2000.
Hijazi "Transcatheter Valve Replacement: A New Era of Percutaneous Cardiac Intervention Begins." J. of Am. College of Cardio; Mar. 2004; 43(6): 1088-1089.
Huber et al. "Do valved stents compromise coronary flow?" European Journal of Cardio-thoracic Surgery; May 2004; vol. 25: 754-759.
Knudsen et al. "Catheter-implanted prosthetic heart valves." Int'l J. of Art. Organs; May 1993; 16(5): 253-262.
Kort et al. "Minimally invasive aortic valve replacement: Echocardiographic and clinical results." Am. Heart J; Sep. 2001; 142(3): 476-481.
Love et al. fThe Autogenous Tissue Heart Valve: Current Stat.f Journal of Cardiac Surgery; Dec. 1991; 6(4): 499-507.
Lutter et al. "Percutaneous aortic valve replacement: An experimental study. I. Studies on implantation." J. of Thoracic and Cardio. Surg; Apr. 2002; 123(4): 768-776.
Moulopoulos et al. "Catheter-Mounted Aortic Valves." Annals of Thoracic Surg; May 1971; 11(5): 423-430.
Paniagua et al. "Percutaneous heart valve in the chronic in vitro testing model." Circulation; Sep. 2002; 106: e51-e52.
Paniagua et al. Heart Watch (2004). Texas Heart Institute. Spring Mar. 2004 Edition: 8 pages.
Pavcnik et al. "Percutaneous bioprosthetic veno valve: A long-term study in sheep." J. of Vascular Surg; Mar. 2002; 35(3): 598-603.
Phillips et al. "A Temporary Catheter-Tip Aortic Valve: Hemodynamic Effects on Experimental Acute Aortic Insufficiency." Annals of Thoracic Surg; Feb. 1976; 21(2): 134-136.
Sochman et al. "Percutaneous Transcatheter Aortic Disc Valve Prosthesis Implantation: A Feasibility Study." Cardiovasc. Intervent. Radiol; Sep.-Oct. 2000; 23: 384-388.
Stuart, M. "In Heart Valves, A Brave, New Non-Surgical World." Start-Up; Feb. 2004: 9-17.
Vahanian et al. "Percutaneous Approaches to Valvular Disease." Circulation; Apr. 2004; 109: 1572-1579.
Van Herwerden et al., "Percutaneous valve implantation: back to the future?" Euro. Heart J; Sep. 2002; 23(18): 1415-1416.
Zhou et al. "Self-expandable valved stent of large size: off-bypass implantation in pulmonary position." Eur. J. Cardiothorac; Aug. 2003; 24: 212-216.
Granada et al.; U.S. Appl. No. 14/677,334 entitled "Replacement cardiac valves and methods of use and manufacture," filed Apr. 2, 2015.
Granada et al.; U.S. Appl. No. 14/677,370 entitled "Replacement cardiac valves and methods of use and manufacture," filed Apr. 2, 2015.
Granada et al.; U.S. Appl. No. 14/677,320 entitled "Replacement cardiac valves and methods of use and manufacture," filed Apr. 2, 2015.

\* cited by examiner

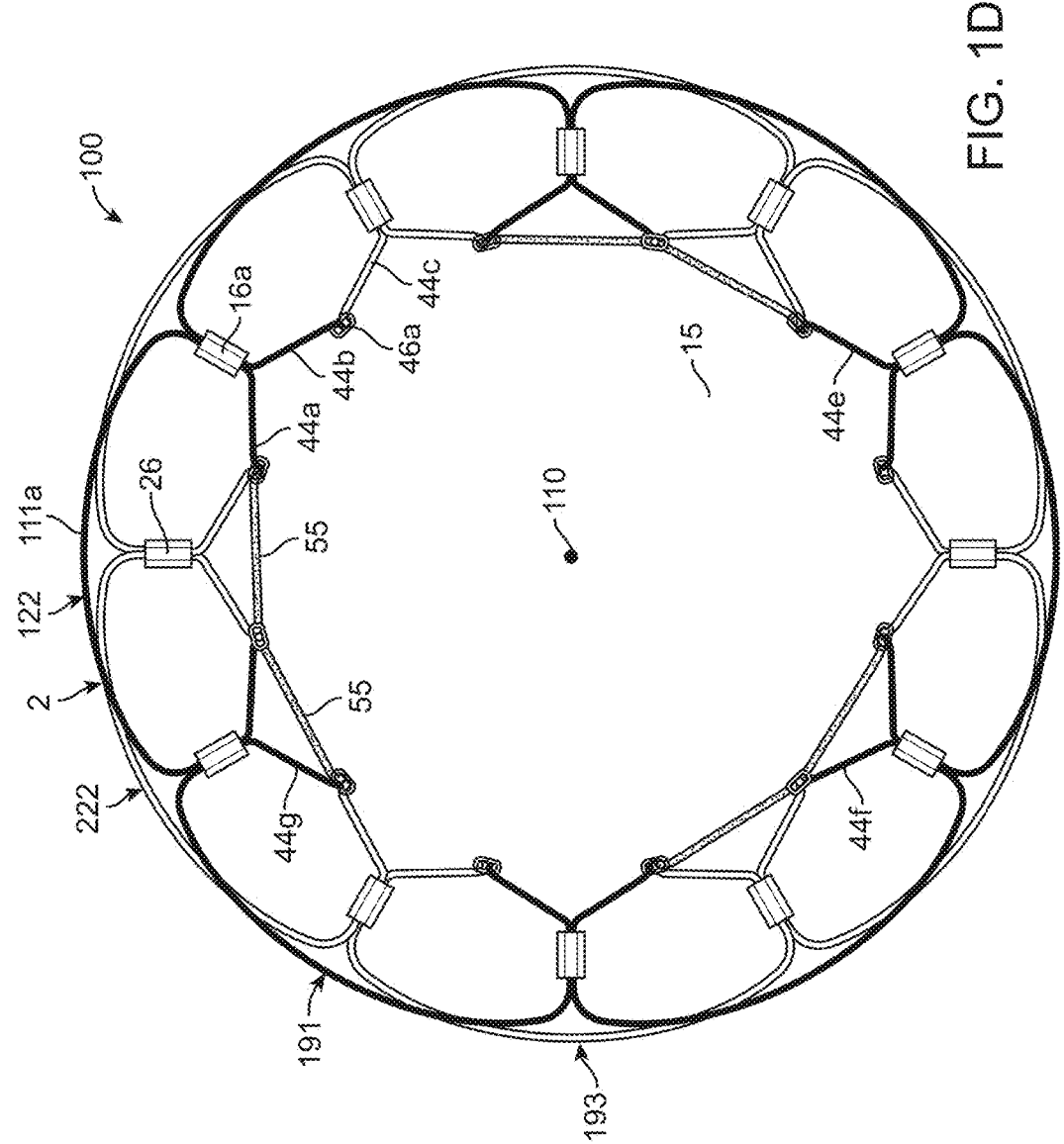

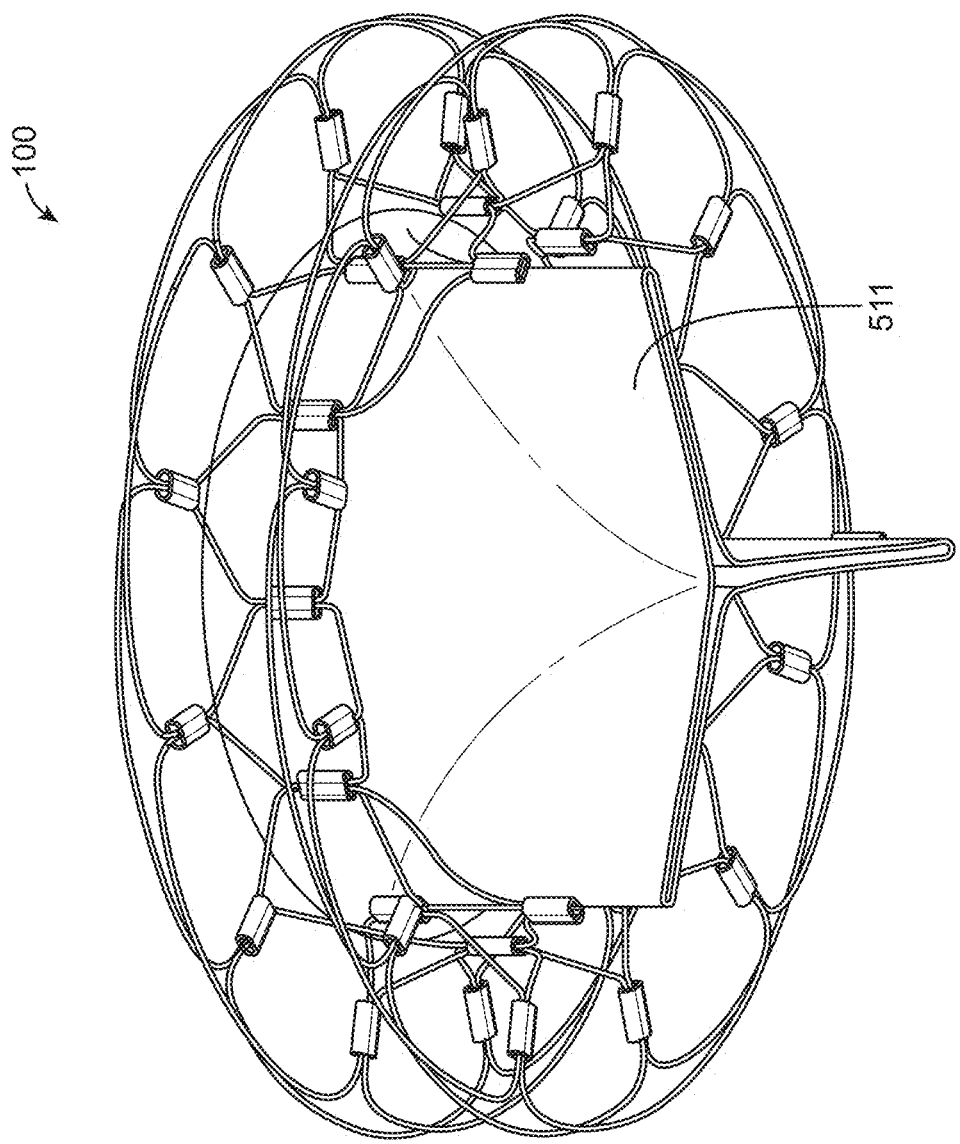

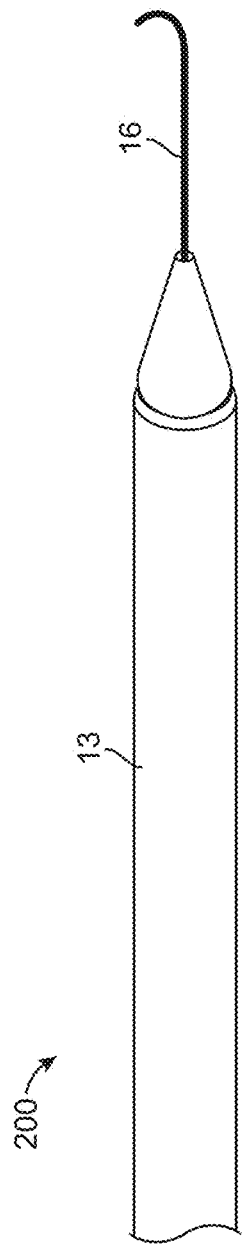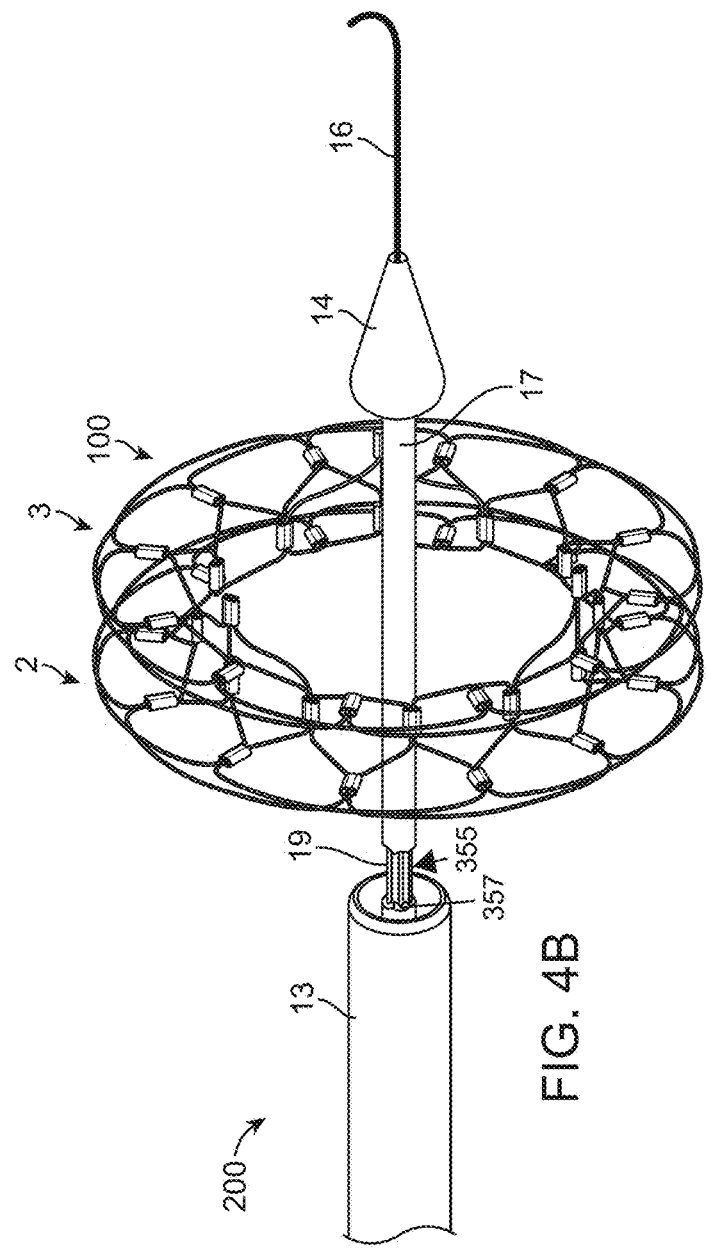
FIG. 4A
FIG. 4B

SYSTEM AND METHOD FOR CARDIAC VALVE REPAIR AND REPLACEMENT

CROSS REFERENCE TO RELATED APPLICATIONS

This application is a continuation of pending U.S. application Ser. No. 14/170,407, filed Jan. 31, 2014, which claims priority to U.S. Provisional Application No. 61/847,515, filed Jul. 17, 2013, both of which are incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

FIELD OF INVENTION

The present invention relates generally to the treatment of cardiac valve disorders, such as mitral valve replacement, using minimally invasive techniques.

BACKGROUND

The mitral valve lies between the left atrium and the left ventricle of the heart. Various diseases can affect the function of the mitral valve, including degenerative mitral valve disease and mitral valve prolapse. These diseases can cause mitral stenosis, in which the valve fails to open fully and thereby obstructs blood flow, and/or mitral insufficiency, in which the mitral valve is incompetent and blood flows passively in the wrong direction.

Many patients with heart disease, such as problems with the mitral valve, are intolerant of the trauma associated with open-heart surgery. Age or advanced illness may have impaired the patient's ability to recover from the injury of an open-heart procedure. Additionally, the high costs are associated with open-heart surgery and extra-corporeal perfusion can make such procedures prohibitive.

Patients in need of cardiac valve repair or cardiac valve replacement can be served by minimally invasive surgical techniques. In many minimally invasive procedures, small devices are manipulated within the patient's body under visualization from a live imaging source like ultrasound, fluoroscopy, or endoscopy. Minimally invasive cardiac procedures are inherently less traumatic than open procedures and may be performed without extra-corporeal perfusion, which carries a significant risk of procedural complications.

Minimally invasive aortic valve replacement devices, such as the Medtronic Corevalve or the Edwards Sapien, deliver aortic valve prostheses through small tubes which may be positioned within the heart through the aorta via the femoral artery or through the apex of the heart. However, current cardiac valve prostheses are not designed to function effectively within the mitral valve. Further, current cardiac valve prostheses delivered via a minimally invasive device are often difficult to place correctly within the native valve, difficult to match in size to the native valve, and difficult to retrieve and replace if initially placed incorrectly.

Accordingly, it is desirable to have a mitral valve replacement that solves some or all of these problems.

SUMMARY OF THE DISCLOSURE

In general, in one embodiment, a prosthetic mitral valve includes a proximal anchor, a distal anchor, and a central portion therebetween. The proximal and distal anchors each include a first outer frame and a second outer frame. The first outer frame includes a plurality of first arcs joined together, and the second outer frame includes a plurality of second arcs joined together. The plurality of first arcs are out of phase relative to the plurality of second arcs.

This and other embodiments can include one or more of the following features. The first plurality of arcs can be movable relative to the second plurality of arcs. The first and second outer frames can be substantially circular. The plurality of first arcs can be disposed around substantially the entire first outer frame, and the plurality of second arcs can be disposed around substantially the entire second outer frame. The plurality of first arcs can lie substantially in a first plane, and the plurality of second arcs can lie substantially in an adjacent second plane. The first and second arcs can be approximately 90 degrees out of phase. The first and second outer frames can be made of wire rope. The wire rope of the first outer frame can have an opposite lay than a lay of the wire rope of the second outer frame. The proximal anchor and distal anchor can be substantially parallel to one another. The central portion can include substructures connecting the proximal and distal anchors. The substructures can be hexagonal. The proximal anchor, distal anchor, and central portion can be configured to expand from a constrained configuration to an expanded configuration. The device can be configured to foreshorten upon expansion of the proximal anchor, distal anchor, and central portion from the constrained configuration to the expanded configuration. The proximal anchor and the distal anchor can each have a diameter in the expanded configuration that is greater than a diameter of the central portion in the expanded configuration.

In general, in one embodiment, a prosthetic mitral valve includes a valve frame comprising a proximal anchor, a distal anchor, and a central portion therebetween. The valve frame is configured to expand from a constrained configuration to an expanded configuration. A plurality of struts is attached to the central portion and extends distally past the distal anchor. A plurality of leaflets are secured to the plurality of struts such that at least a portion of each leaflet extends distally past the distal anchor.

This and other embodiments can include one or more of the following features. The valve frame can be configured to self-expand. The plurality of leaflets can be attached to the central portion. The plurality of leaflets can include a biomaterial or a polymer. The proximal anchor can be covered with a skirt configured to seal the prosthetic valve. The skirt can include a biomaterial or polymer. The outer perimeter of the proximal anchor can be substantially circular when covered with the skirt. The plurality of leaflets can be arranged to fill an inner diameter of the mitral valve prosthetic. The ratio of the inner diameter to a height of the plurality of struts can be approximately 2:1. The valve frame can be configured to foreshorten upon expansion of the valve frame from the constrained configuration to the expanded configuration. The proximal anchor and the distal anchor can each have a diameter in the expanded configuration that can be greater than a diameter of the central portion in the expanded configuration.

In general, in one embodiment, a prosthetic mitral valve includes a valve frame having a proximal anchor, a distal anchor, and a central portion therebetween. The valve frame is configured to expand from a constrained configuration to an expanded configuration. The ratio of an outer diameter of the central portion to a length of the valve frame in the expanded configuration is at least 1.1.

This and other embodiments can include one or more of the following features. The valve frame can be configured to self-expand. The ratio can be less than or equal to 2. The ratio of the outer diameter of the proximal anchor or the distal anchor to the length of the device can be greater than or equal to 2. The outer diameter of the central portion can be between 25 and 40 mm. The length can be less than or equal to 22 mm. The proximal and distal anchors can extend radially outward from the central portion. The outer diameter of the proximal and distal anchors can be at least 38 mm.

In general, in one embodiment a method of delivering a prosthetic mitral valve includes delivering a distal anchor from a delivery sheath such that the distal anchor self-expands inside a first heart chamber on a first side of the mitral valve annulus, pulling proximally on the distal anchor such that the distal anchor self-aligns within the mitral valve annulus and the distal anchor rests against tissue of the ventricular heart chamber, and delivering a proximal anchor from the delivery sheath to a second heart chamber on a second side of the mitral valve annulus such that the proximal anchor self-expands and moves towards the distal anchor to rest against tissue of the second heart chamber. The self-expansion of the proximal anchor captures tissue of the mitral valve annulus therebetween.

This and other embodiments can include one or more of the following features. The first heart chamber can be a ventricular heart chamber, and the second heart chamber can be an atrial heart chamber.

In general, in one embodiment, a method of delivering a prosthetic mitral valve includes securing a prosthetic valve within a delivery device by extending a plurality of wires of the delivery device through a proximal anchor so as to collapse the proximal anchor, extending the prosthetic delivery device into a heart with the prosthetic valve covered by a sheath of the delivery device, pulling the sheath proximally to expose a distal anchor of the prosthetic valve, thereby allowing the distal anchor to self-expand into place on a first side of the mitral valve annulus, pulling the sheath proximally to expose the proximal anchor, loosening the wires of the delivery device so as to allow the proximal anchor to self-expand into place on a second side of the mitral valve annulus, and removing the delivery device from the heart.

This and other embodiments can include one or more of the following features. The method can further include tightening the wires after loosening the wires so as to collapse the proximal anchor again, repositioning the proximal anchor to a second location on the second side of the mitral valve annulus and loosening the wires of the delivery device so as to allow the proximal anchor to self-expand into place at the second location on the second side of the mitral valve annulus. Extending a plurality of wires of the delivery device through a proximal anchor so as to collapse the proximal anchor and can include extending a plurality of wires through arcs of the proximal anchor. Neighboring retention wires can extend through neighboring arcs. The method can further include extending a guidewire down a central lumen of the delivery device before extending the prosthetic delivery device into the heart. Tightening and loosening the wires of the delivery device can be performed with a control on a handle of the delivery device.

In general, in one embodiment, a delivery device includes a central longitudinal structure having a plurality of tubes extending therethrough, a retention wire extending within each tube, a sheath, a handle, and a control on the handle. Each tube has a tubular wall and an aperture in the tubular wall. Each retention wire configured to extend through a portion of a medical device at the aperture. The sheath is configured to fit over and slide relative to the central longitudinal structure and the medical device. The handle is connected to the central longitudinal structure. The control on the handle is configured to tighten the wires to collapse at least a portion of the medical device and to loosen the wires to expand the portion of the medical device.

This and other embodiments can include one or more of the following features. The delivery device can further include a central lumen extending through the central longitudinal structure. The central lumen can be configured to house a guidewire. The retention wires can be made of nitinol or liquid crystal polymer fiber. There can be between 4 and 20 retention wires and tubes. The delivery device can further include a tapered distal tip connected to the central longitudinal structure. The control can be further configured to retighten the wires after loosening to collapse the portion of the medical device again.

BRIEF DESCRIPTION OF THE DRAWINGS

The novel features of the invention are set forth with particularity in the claims. A better understanding of the features and advantages of the present invention will be obtained by reference to the following detailed description that sets forth illustrative embodiments, in which the principles of the invention are utilized, and the accompanying drawings of which:

FIGS. 1A-1E are various view of a compliant, self-centering valve prosthesis structure suitable for delivery via minimally invasive surgical techniques. FIGS. 1A and 1B are isometric views of the prosthesis. FIG. 1C is a proximal view of a proximal anchor of the prosthesis. FIG. 1D is a proximal view of the prosthesis. FIG. 1E is a side view of the prosthesis.

FIGS. 2A-2C show an exemplary prosthesis with leaflets attached thereto. FIG. 2A is an isometric view of the prosthesis. FIG. 2B is a distal view of the prosthesis. FIG. 2C is a section view of the prosthesis.

FIG. 3A is a proximal view of the prosthesis. FIG. 3B is a side view of the prosthesis.

FIG. 4A shows a delivery device with a prosthesis fully loaded therein. FIG. 4B shows the delivery device with the prosthesis deployed.

FIG. 5A shows a delivery device housing the prosthesis. FIG. 5B shows the distal anchor of the prosthesis deployed with the proximal anchor folded up therearound. FIG. 5C shows the sheath of the delivery device pulled back to expose the retention wires of the delivery device. FIG. 5D shows the valve prosthesis fully deployed around the delivery device.

FIG. 12A shows the use of twelve retention wires. FIG. 12B shows the use of six retention wires.

DETAILED DESCRIPTION

Figure 1A:
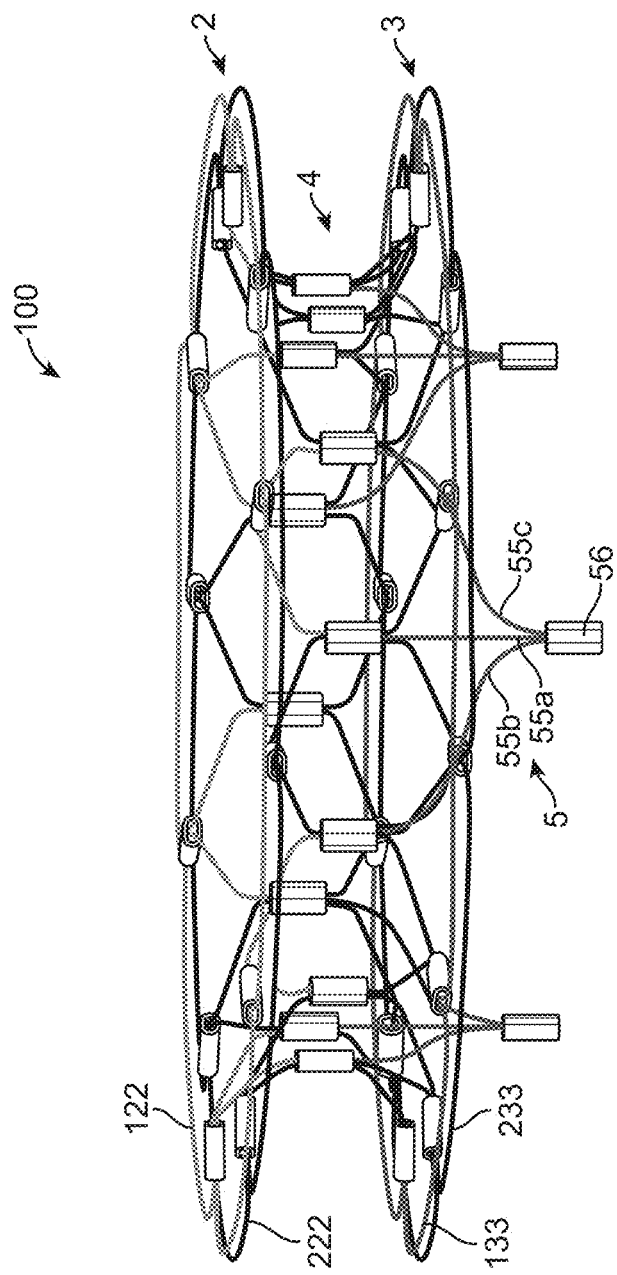
Figure 1B:
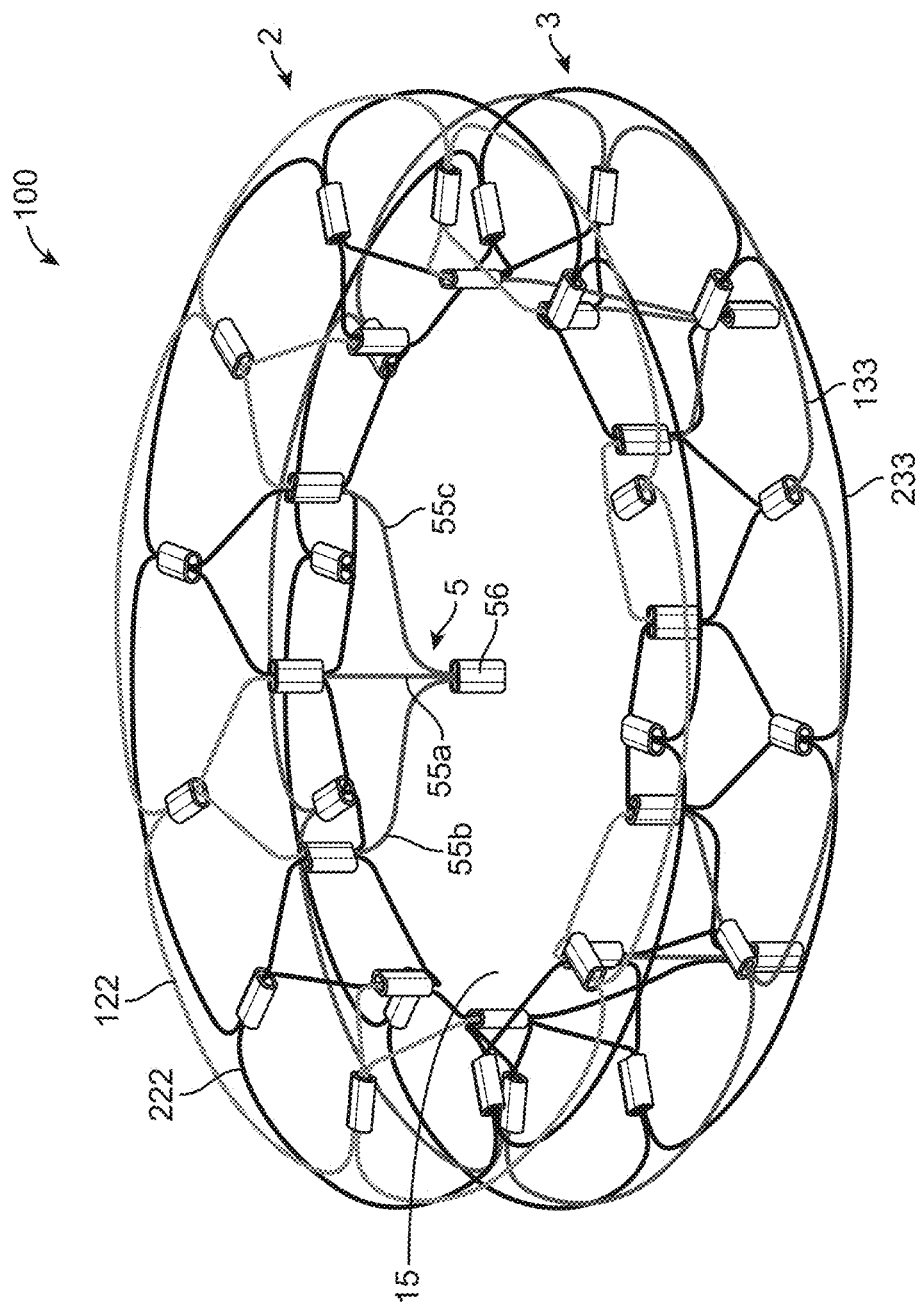

Described herein is a flexible, self-orienting cardiac valve prosthesis configured to be delivered through minimally invasive techniques. The prosthesis can include a proximal anchor (e.g., configured to be placed in the ventricle), a distal anchor (e.g., configured to be placed in the atrium), a central portion or column between the anchors, a plurality of struts extending distally (e.g., into the ventricle), and a plurality of leaflets attached to the struts. The prosthesis can be self-expanding, such as be made of super elastic nickel titanium (nitinol). In some embodiments, the prosthesis can be made of woven stranded nitinol.

The prosthesis described herein can be delivered to a cardiac valve orifice, such as the mitral valve, by using minimally invasive techniques to access cardiac valves through small incisions in the patient's body, passing the prosthesis through the apex of the heart, through the aorta via femoral artery access, through the aorta via an intercostal puncture, through the vena cava via femoral vein access, through the vena cava via jugular access, and through the venous system into the left heart via a transseptal puncture. The flexible prosthesis can be folded and compressed to fit within a delivery tube. The delivery tube can used to position the prosthesis at the treatment site, and if necessary, re-sheath, reposition, and re-deploy the device.

During deployment, the distal anchor can be deployed first in a cardiac chamber, such as the ventricle, and retracted to a seated position against the valve orifice, such as the mitral valve orifice. Then the center column and proximal anchor may then be deployed in another cardiac chamber, such as the atrium, sandwiching the valve orifice securely between the anchors in opposing cardiac chambers.

Embodiments of the invention are designed to secure the valve prosthesis in the orifice by applying a radial force from the center column structure of the prosthesis outward against the cardiac orifice and by sandwiching the cardiac orifice between distal and proximal anchors that are larger in diameter than the orifice. Further engagement between the prosthesis and tissue may be added by securing small, curved wire hooks into the sub-structures of the valve prosthesis.

FIGS. 1A-1E show an exemplary embodiment of a valve prosthesis 100. The valve prosthesis includes a proximal anchor 2, a distal anchor 3, and a central portion 4 therebetween. A central opening 15 extends through the center of the prosthesis 100. The central portion 4 can substantially trace the perimeter of the central opening 15 while each anchor 2, 3 can extend outwardly therefrom in an annular shape. The proximal anchor 2, distal anchor 3, and central portion 4 can be formed of wire, such as nitinol wire rope. Each anchor 2,3 can include a first outer frame 122, 133 and a second outer frame 222, 233, respectively. In one embodiment, the proximal anchor 2 and distal anchor 3 can be substantially parallel to one another.

Figure 1C:
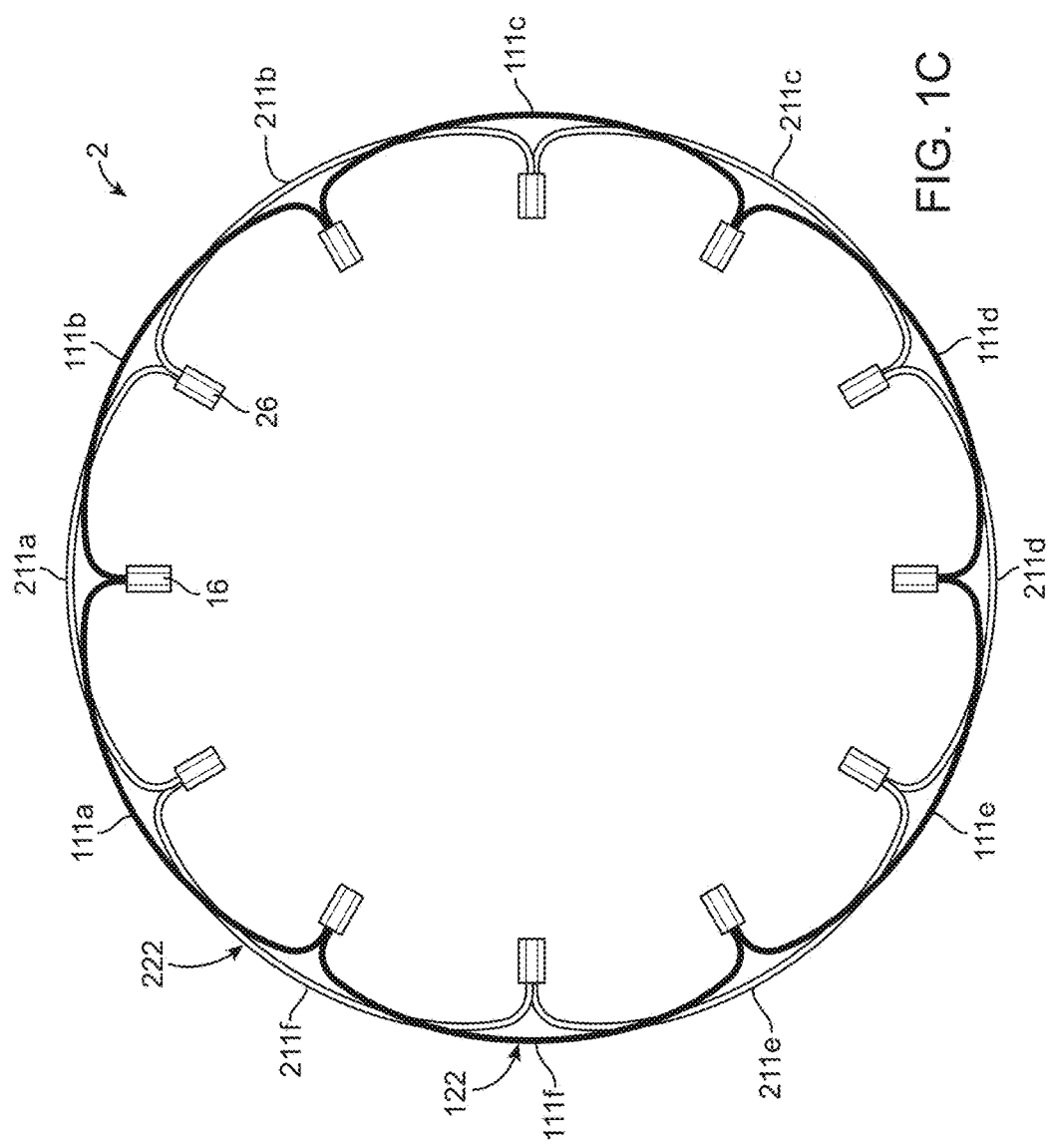

An exemplary proximal anchor 2 is shown in FIG. 1C. The first outer frame 122 can sit proximal to the second outer frame 222, and the first outer frame 122 can sit in a plane substantially parallel to the plane of the second outer frame 222. Further, each frame 122, 222 can include a plurality of arcs 111, 211 (which can also be referred to as arcuate portions, curved portions, or petals), such as between 4 and 10 or between 5 and 8 arcs, joined together at joints 16, 26, respectively. For example, outer frame 122 can include six arcs 111$a,b,c,d,e,f$ while outer frame 222 can also include six arcs 211$a,b,c,d,e,f$. The arcs 111 of the outer frame 122 can be connected together, and the arcs 211 of the outer frame 222 can be connected together, so as to form a substantially circular outer perimeter for each of the frames 122, 222.

Each joint 16, 26 between neighboring arcs 111 or 211 can be, for example, a crimp that crimps adjacent arcs (e.g., 111$a$ and 111$b$) to one another. As shown in FIG. 1C, the outer frames 122, 222 can be positioned relative to one another such that the arcs 111, 211 are out of phase relative to one another. For example, the arcs 111 can be approximately 90 degrees out of phase relative to the arcs 211. That is, the arcs 111 of the first outer frame 122 can overlap with the arcs 211 of the second outer frame 222 such that, for example, a single arc 111$a$ of the first outer frame 122 overlaps with half of two underlying arcs 211$f$, 211$a$ of the second outer frame 222. In some embodiments, only some arcs are out of phase with one another while other arcs are in-phase with one another. The second outer frames 133, 233 can likewise include arcs as described with respect to the first outer frame 122, 222.

Figure 1E:
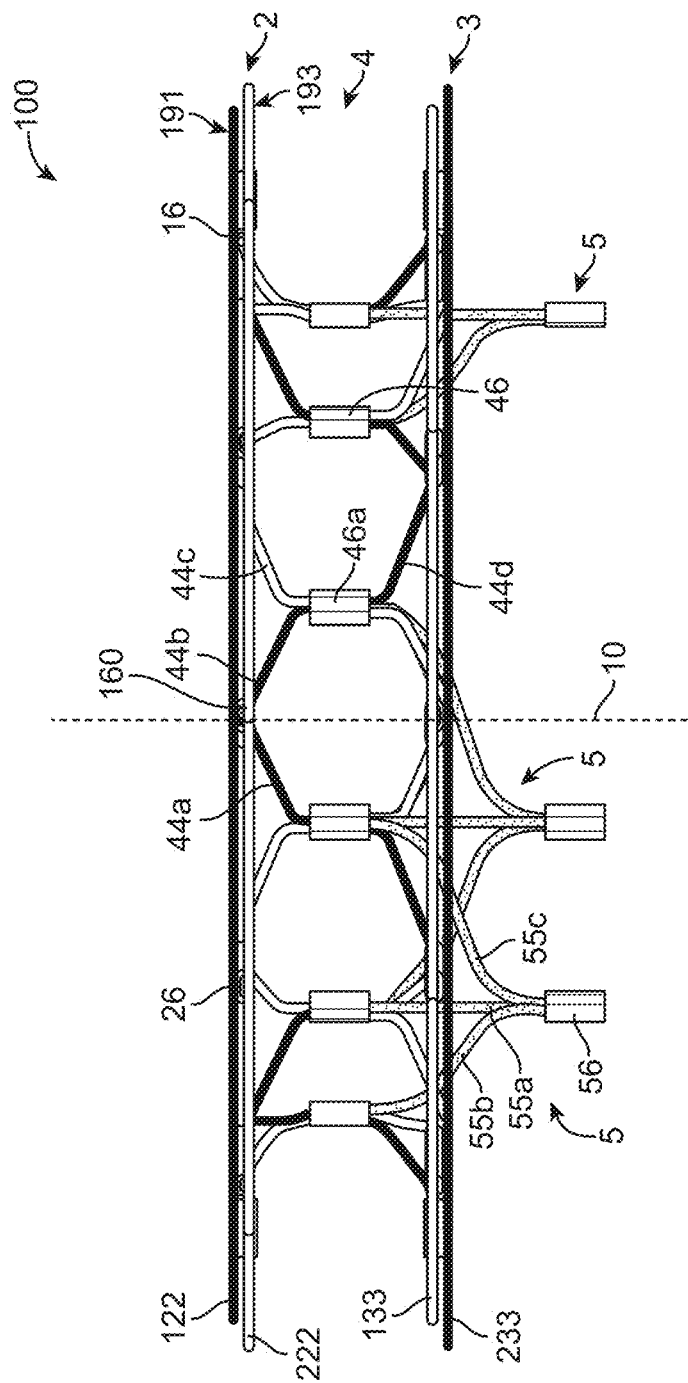

As shown in FIGS. 1A and 1E, the first outer frame 122, 133 and the second outer frame 222, 233 of each anchor 2, 3 can be connected to one another through the central portion 4. The central portion 4 can extend from the crimps 16, 26 of the proximal anchor 2 to the corresponding crimps of the distal anchor 3. The central portion 4 can include substructures or wire segments 44 that form a pattern, such as a hexagonal pattern (see FIG. 1E). For example, two wire segments 44$a,b$ of the central portion 4 can extend at an angle from the crimp 16$a$ (see FIGS. 1D, 1E), such as to form an angle of approximately 120 degrees relative to one another. Each of the wire segments 44$a,b$ can then meet adjacent wire segments within the central portion 4 (e.g., segment 44$b$ meets segment 44$c$). The adjacent wire segments (e.g., 44$b$ and 44$c$) can then be joined together at a joint 46 (e.g., joint 46$a$). The joint 46$a$ can form a column substantially parallel to a central axis 110 of the prosthesis 100. This pattern can extend throughout the entire prosthesis to form a number of joints 46, such as twelve joints 46. The joints 46 can not only fix the position of the outer frames of a single anchor together, but also fix the proximal and distal anchors 2, 3 together. The hexagonal structure of the segments 44 and joints 46 can advantageously provide radial and vertical strength as well as stability to the prosthesis 100.

In some embodiments (as shown in FIG. 1D), parts of the central portion 4 can be formed of the same wire or wire rope as the outer frames of the anchors 2,3 and/or the outer frames of the anchors 2,3 can be formed of the same wire or wire rope as one another. For example, two single strands of wire, such as two 22-inch long strands of wire, can be used to form the anchors 2, 3 and the central portion 4. As shown in FIGS. 1D and 1E, a single strand 191 (darkened in the picture relative to the opposite strand 193 for clarity) can foam an arc 111$a$ (see FIG. 1D) of the first outer frame 122 of proximal anchor 2, extend through a joint 16$a$ to form wire segment 44$b$ of the central portion 4, extend through joint 46$a$ to form wire segment 44$d$ (see FIG. 1D), then form an arch of the second outer frame 233, extend through another joint to form wire segment 44$e$ (see FIG. 1D), extend around in a similar fashion to form wire segment 44$f$ (see FIG. 1D), and continue winding in a similar fashion until all of the outer frames 122, 233 have been formed from the single strand 191. The ends of the strand 191 can then be attached to one another, such as through splicing crimps, butt joint crimps, welding, riveting, or weaving. The second strand 193 can be wound similarly to form the second outer frame 222 of the proximal anchor 2 and the first outer frame 133 of the distal anchor 3.

By joining the first outer frame 122, 133 to the second outer frame 222, 233 of each anchor 2, 3, as described above, the arcs of each outer frame can be movable relative to one another. For example, the arc 111a can be movable relative to the arcs 211f, 211a that it overlaps (see FIG. 1C). That is, the outer perimeter of the arc 111a can flex along the central axis and/or translate relative to the arcs 211f, 211a (while the inner perimeter is fixed at the joints 46).

Advantageously, the large arc structure of the anchors can provide flexibility and compliance for the portions of the prosthesis intended to be placed in the chambers of the heart. In contrast, in the stiffer tissue of the valve orifice, the hexagonal sub-structures of the central portion can provide higher radial stiffness and strength.

Further, by using wire rope, the prosthesis can advantageously be foldable and strong while the individual fibers, because they are small in diameter, can maintain resistance to fatigue and fracture. In some embodiments, the two frames of a single anchor can be formed of wire rope of opposite lays. For example, the wire of one frame (e.g., strand 193) can be made of a rope twisted to the left while the wire of another frame (e.g., strand 191) can be made of a rope twisted to the right. Using wires of opposite lays can allow the wires to compensate for one another as they compress, thereby maintaining relative positioning during expansion or contraction/folding of the device (as opposed to twisting of the entire device). Various possibilities for winding the wire rope are shown in FIGS. 8A-9B.

Figure 2B:
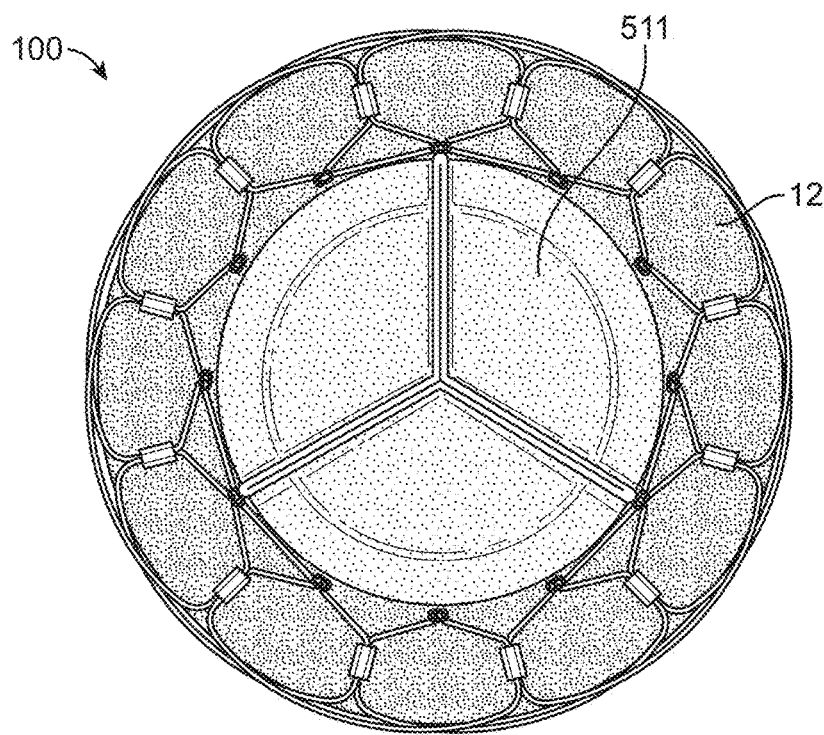
Figure 2C:
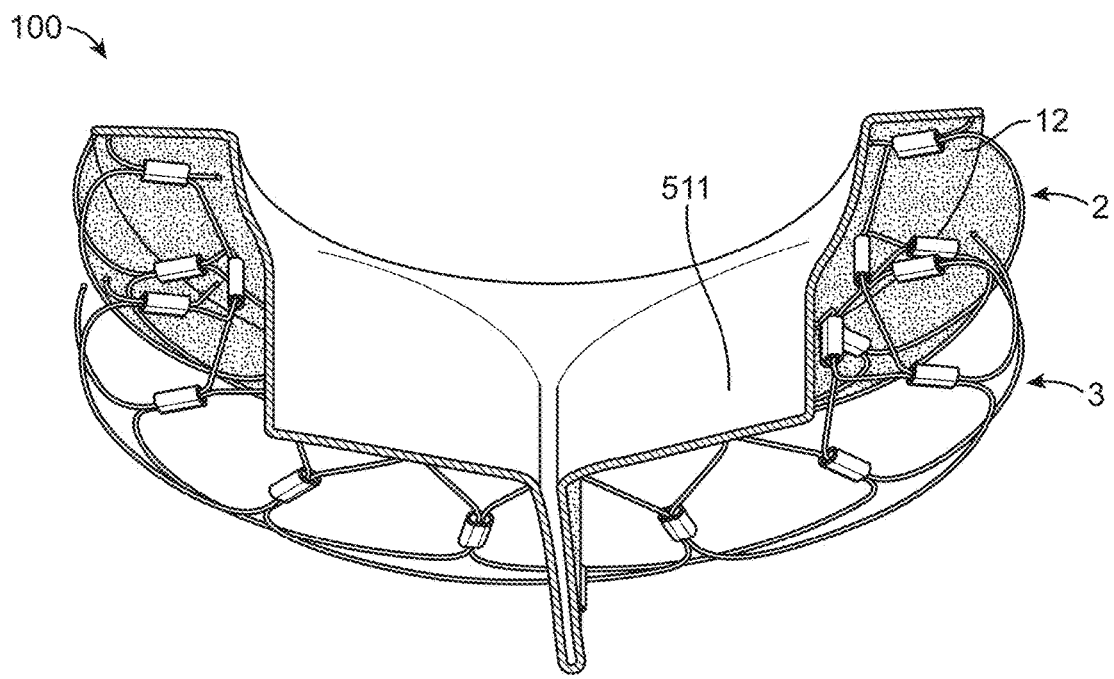

As shown in FIGS. 1A and 1E, struts 5 can extend distally from the distal anchor 3 and/or the central portion 4 and be configured to hold leaflets (shown in FIGS. 2A-2C). The struts 5 can be formed, for example, of wire rope. Further, in one example, each strut 5 can include a plurality of wire components 55, such as three wire components 55. Each of the three wire components 55 of a single strut 5 can extend from neighboring joints 46 and come together at a joint 56, thereby forming triangular struts 5. In some embodiments, additional supporting structures, such as tubes, can be placed over or around the struts to increase the stiffness. The triangular struts 5 can provide vertical strength and lateral flexibility.

In one embodiment, there can be three struts 5 located approximately 120 degrees away from one another around the circumference of the prosthesis 100. The joints 56 can be, for example, crimps. As shown in FIGS. 1A and 1E, in one embodiment, the center strut member 55a of a three-strut support can be substantially straight and connected to two outside, curved strut members 55b, 55c to form a structure comprised of two substantially triangular sub-structures, each with the center member as a common triangle leg. This center member may be made of a thin element of material which provides strength in tension as the pressurized leaflets are pushed toward the center of the valve, while providing flexion in compression to allow the valve prosthesis to be folded for delivery and to allow the prosthesis to conform to tissue when placed within the heart.

The various crimps used for the joints of the prosthesis 100 may be made of a suitable implantable material, such as platinum, tantalum, or titanium. Further, in place of crimps, braids, weaves, or welding can be used.

Referring to FIGS. 2A-2C, the valve prosthesis 100 can include integral valve leaflets 511 attached, such as sewn, to the struts 5. There can be three integral valve leaflets 511, and the leaflets 511 can form a pressure actuated valve that provides uni-directional flow occlusion when the prosthesis 100 is implanted in a valve orifice. The leaflets can be constructed of bio-materials, such as bovine or porcine pericardium, or polymer materials.

In one embodiment (shown in FIGS. 2B-2C), the proximal anchor 2 can include a cover or skirt 12 thereon or therearound formed of a biomaterial or thin polymer material. The skirt 12 can advantageously help seal the prosthesis 100 against the cardiac tissue when implanted.

The prosthesis 100 can be configured to be placed in a cardiac valve orifice such that the central portion 4 lines the orifice while the proximal and distal anchors 2, 3 sit within the chambers of the heart and pinch tissue of the orifice therebetween.

Figure 3A:
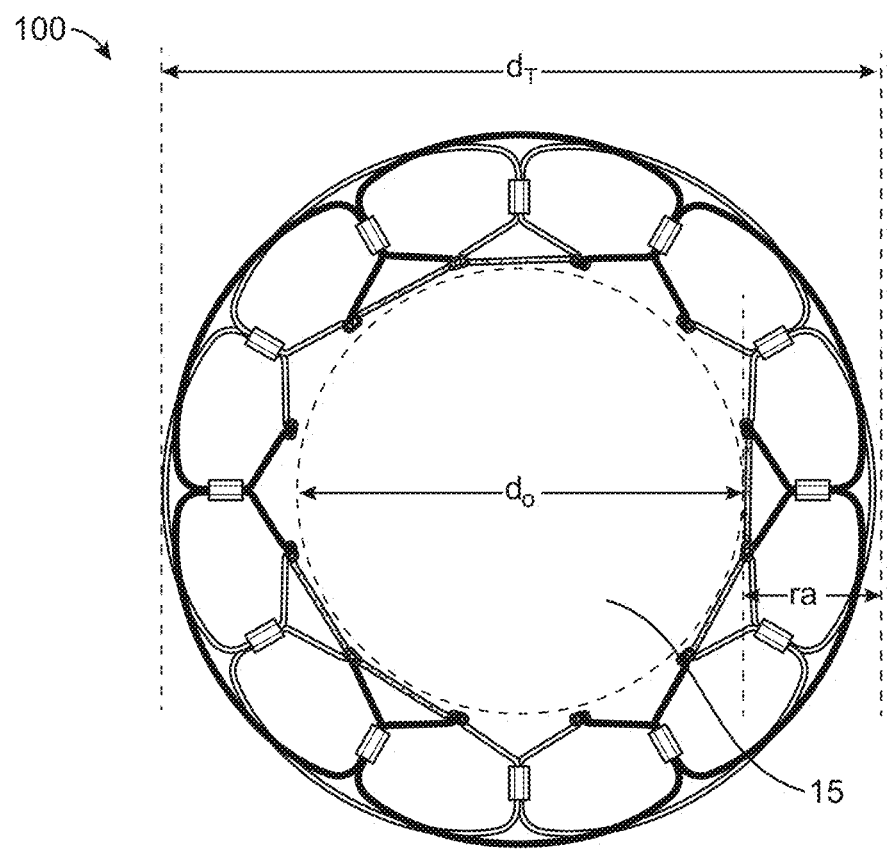
FIGS. 3A-3B show the prosthesis of FIGS. 1A-1E with various dimensions marked thereon.
Figure 3B:
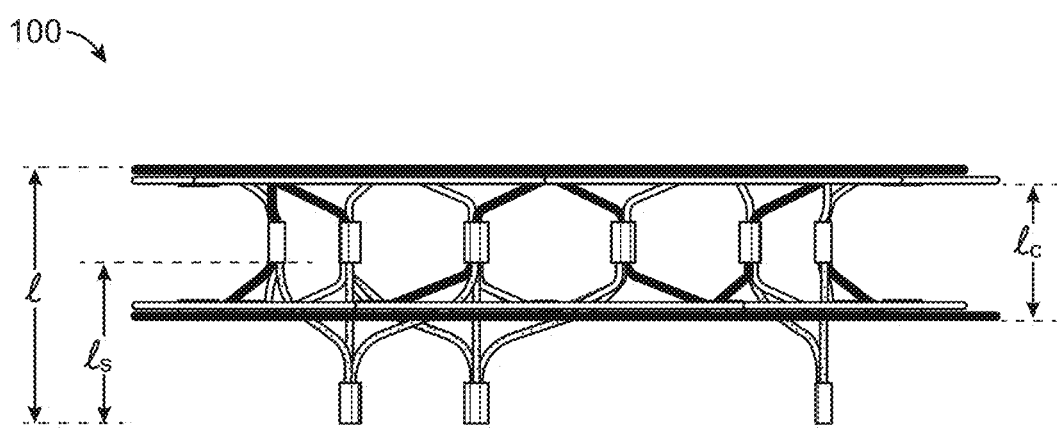
Figure 6A:
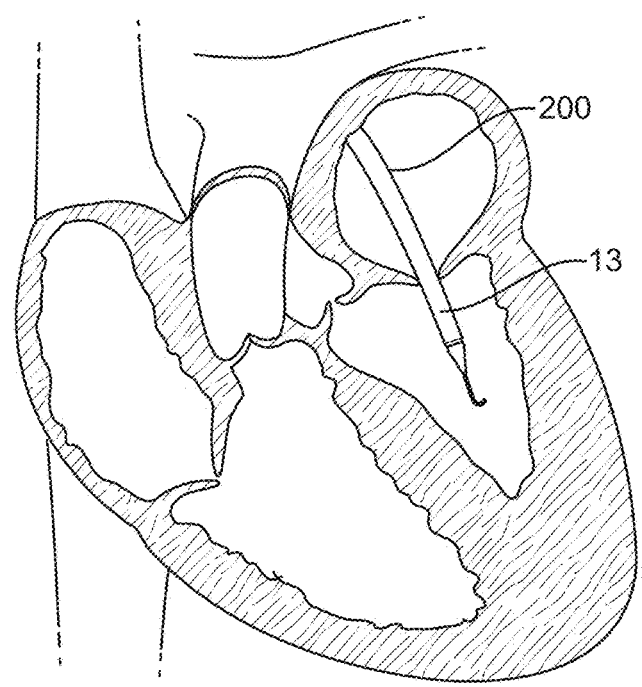
FIGS. 6A-6D show placement of a prosthesis within the mitral valve using a delivery device.
Figure 6B:
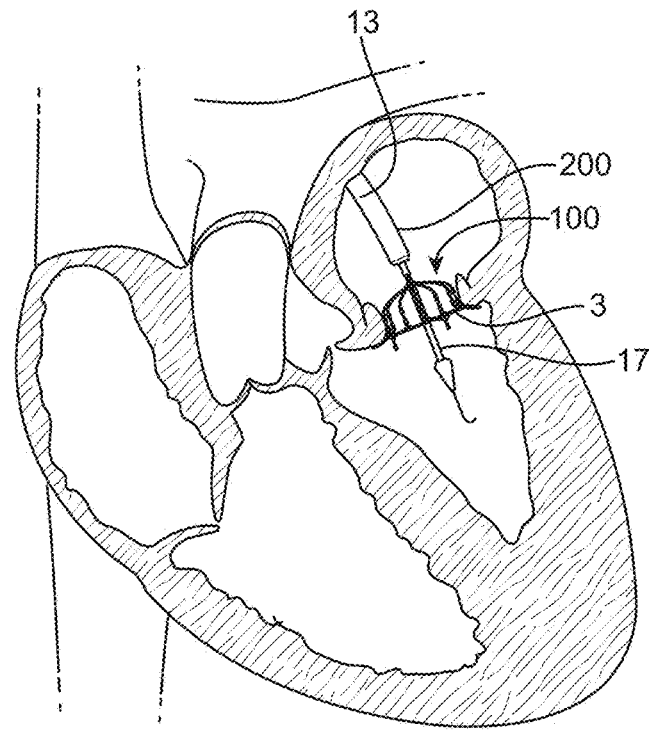
Figure 6C:
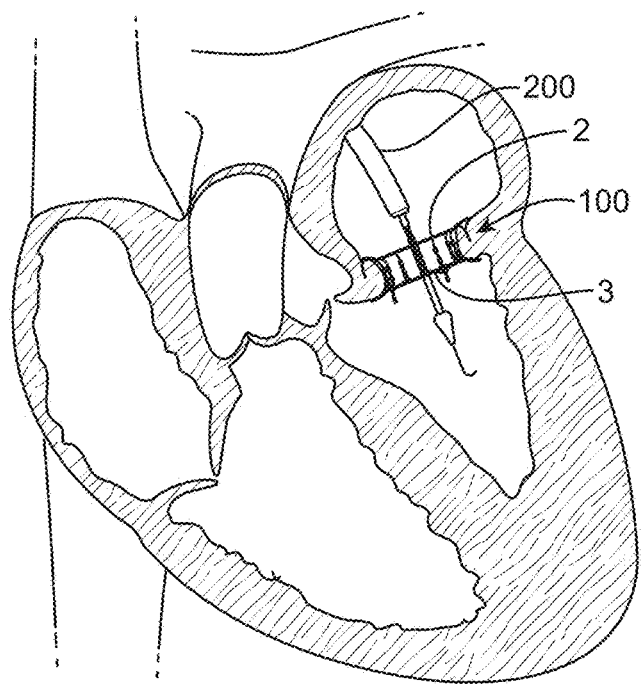
Figure 6D:
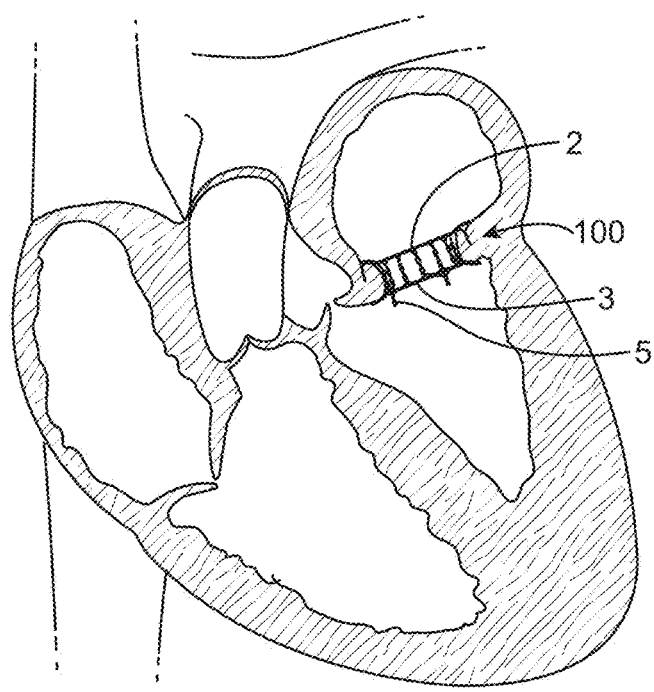

In some embodiments, the prosthesis 100 can be sized and configured for use in the mitral valve orifice (shown in FIG. 6D). Referring to FIGS. 3A-3B, to ensure that the prosthesis 100 fits properly within the valve, the diameter $d_o$ of the central opening 15 can be greater than a length l of the device when fully expanded. For example, the ratio $d_o/l$ can be greater than or equal to 1.1, such as greater than or equal to 1.2 or greater than or equal to 1.3. Further, the ratio $d_o/l$ can be less than 2.0. In one embodiment, the diameter $d_o$, is between 25 mm and 40 mm, such as approximately 28 mm. Further, in one embodiment, the length l is less than or equal to 22 mm, or less than or equal to 20 mm, such as approximately 14 mm. Further, to ensure that the proximal and distal anchors have enough tissue to grab onto, a ratio of the outer diameter of the anchors, $d_T$, to the length l can be greater than or equal to 2.0. In one embodiment, an outer diameter of anchors, $d_T$, can be at least 38 mm, such as greater than or equal to 40 mm. Further, in one embodiment, the anchors can extend out at a radius $r_a$ of greater than 10 mm, such as approximately 12 mm. Finally, a ratio $d_o$ to a length of the struts $l_s$ can be approximately 1.5 to 3.0, such as 2.1. A radio of $d_o/l_s$ within this range can advantageously ensure that there is enough leaflet material to allow the leaflets to oppose and seal under stress while maintaining a small enough length to fit properly within the valve. In one embodiment, the struts have a length $l_s$ of between 8 and 16 mm, such as approximately 14 mm. Further, $l_c$ can be approximately 4-10 mm, such as 6 mm.

In one exemplary embodiment, $d_o$ is 28 mm, $r_a$ is 12 mm, $l_c$ is 6 mm, $l_s$ is 14 mm, $d_T$ is 40 mm, and l l is 14 mm.

FIGS. 4A-4B show a closed delivery device 200 for delivery of a valve prosthesis 100. The delivery device 200 can include an outer sheath 13 and a multi-lumen central longitudinal structure 17 extending therethrough. The valve prosthesis 100 is configured to fit over the central longitudinal structure 17 and within the sheath 13 so as to be fully encapsulated within the delivery device 200. The lumens in the longitudinal structure 17 can be tubular structures 357 (see FIGS. 4B and 5C). Each tubular structure 357 can include a side lumen 355 (see FIGS. 4B and 10A) therein, i.e., an aperture disposed on a radial outer portion of the tubular wall. The tubular structures 357 can contain retention members 19 that bind the proximal anchor 2 of the valve prosthesis tightly to the longitudinal structure 17. The retention members 19 can be made, for example, of a strong, flexible material such as nitinol, nitinol wire rope, or liquid crystal polymer fiber, such as Vectran®. There can be various numbers of retention wires and corresponding tubes 357 and lumens, such as between 4 and 20 or between 6 and 12 retention wires and corresponding tubes/lumens. In one embodiment, there are six retention wires and lumens. In another, there are twelve retention wires and lumens. The delivery device 200 includes a central lumen 15 running therethrough (i.e., through the central longitudinal structure 17) configured to pass a standard cardiac guidewire 16. The guidewire 16 may be used to provide a safe pathway for getting the device 100 to the anatomical target. The delivery device 200 further includes a tapered tip 14 to provide a gradual, atraumatic transition from the guidewire to the outer sheath 13 of the delivery device 200.

In some embodiments, the delivery device 200 can be adapted to specific delivery paths and cardiac structures by being provided with pre-shaped bends in the outer sheath 13. In some embodiments, the delivery device 200 may contain pull-wires integral with the outer wall that may be tensioned to articulate and bend the outer sheath 13. The pull wires may terminate at the tip of the device to provide a bend starting at the distal tip or may terminate along the longitudinal shaft of the device to provide a more proximal bend location.

Figure 5A:
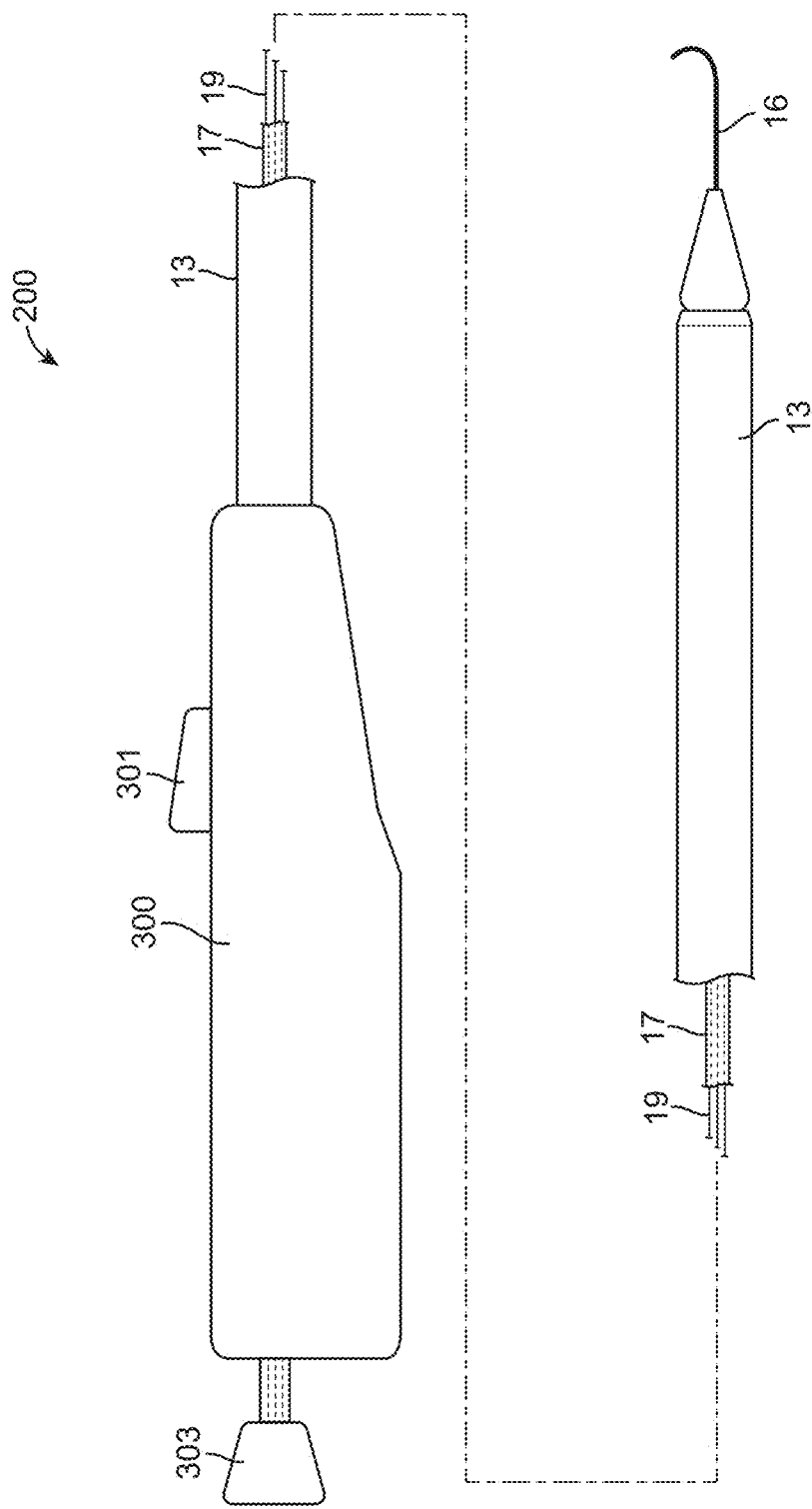
FIGS. 5A-5D shows exemplary steps for delivery a valve prosthesis.

FIGS. 5A-5D show a multi-stage delivery system for a cardiac valve prosthesis (with the valve leaflets omitted from the drawings for clarity). FIG. 5A shows the delivery device 200 having a handle 300 connected thereto to control the delivery of a prosthesis loaded within the device.

Figure 5B:
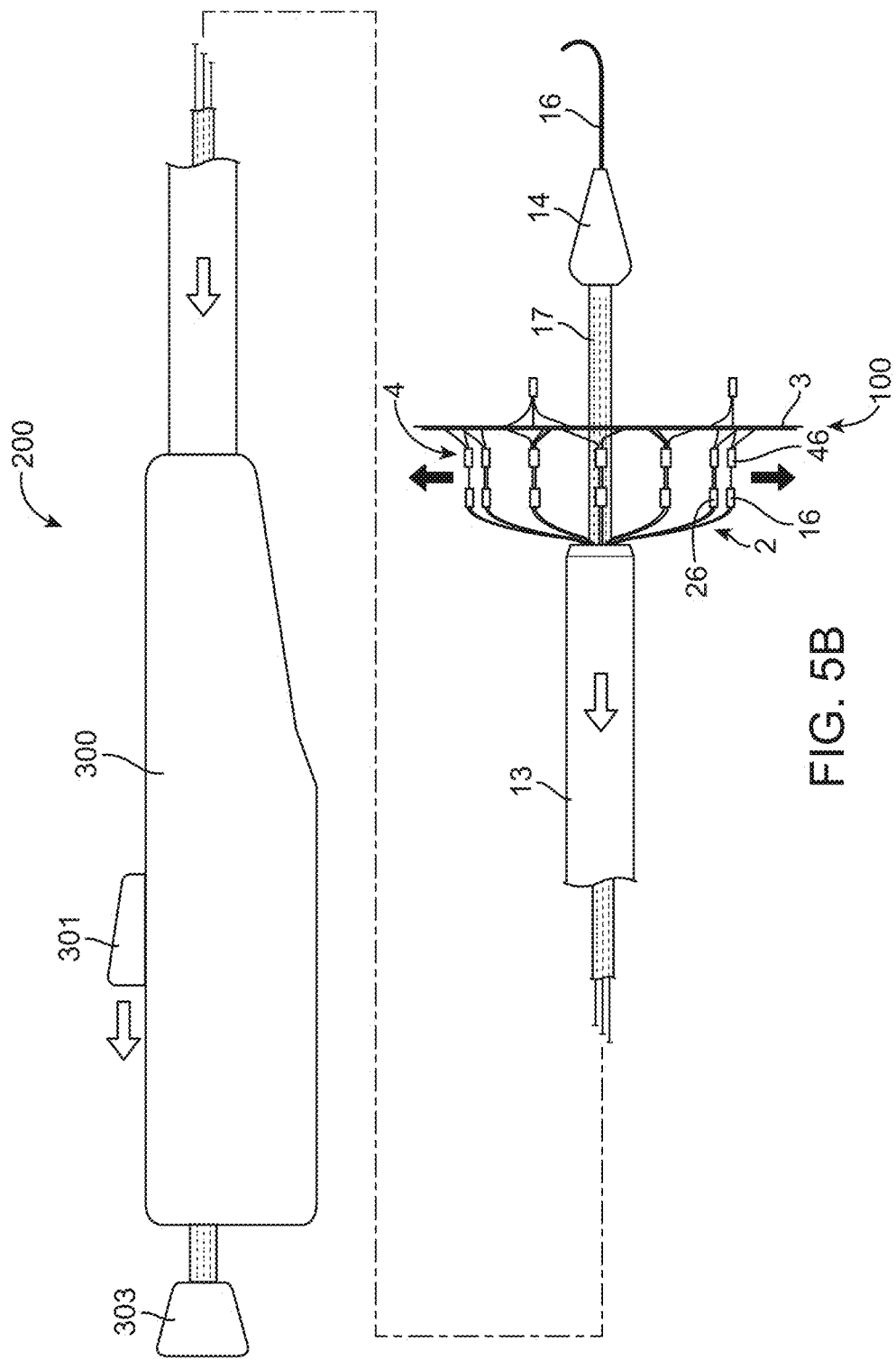
Figure 5C:
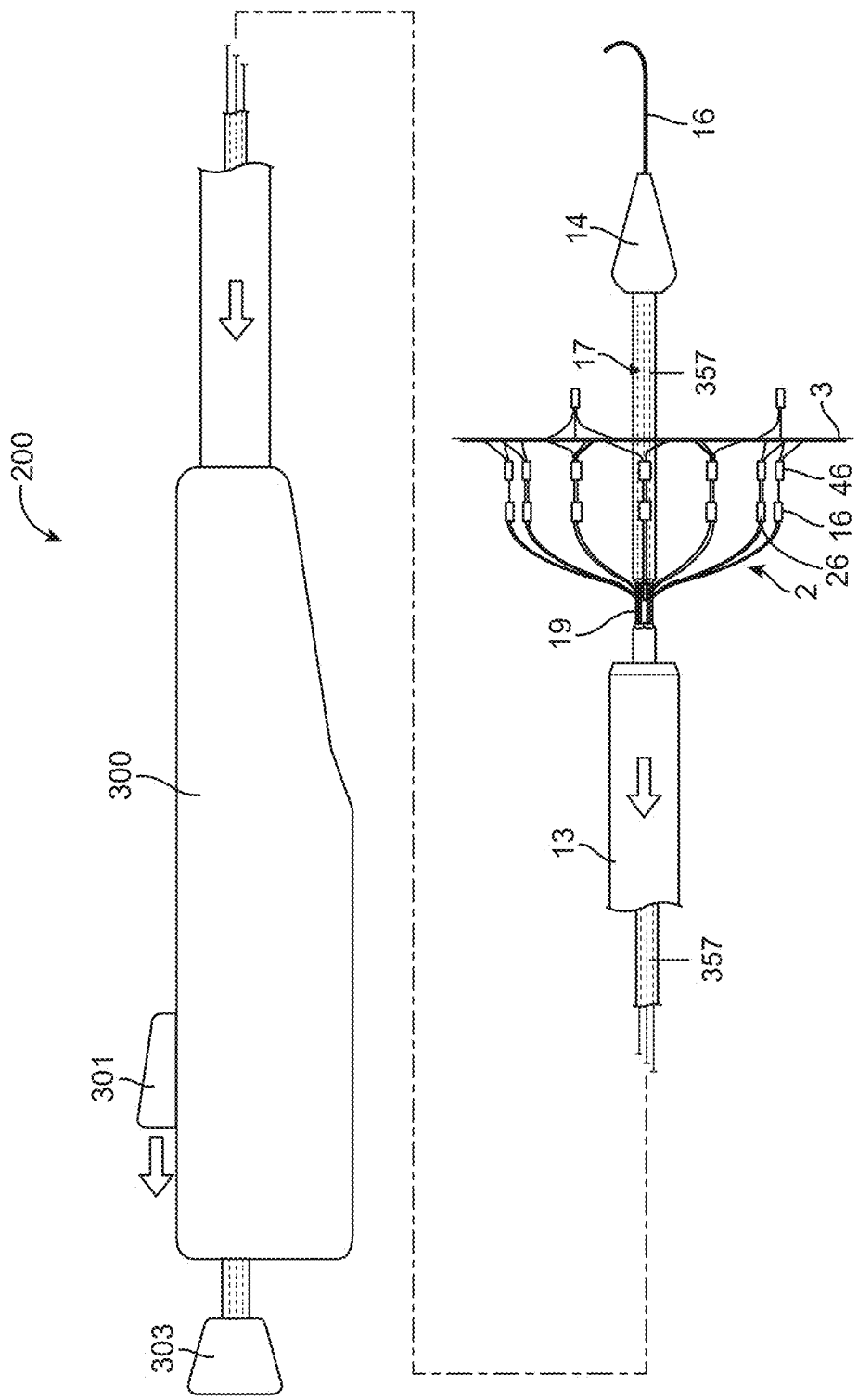
Figure 10A:
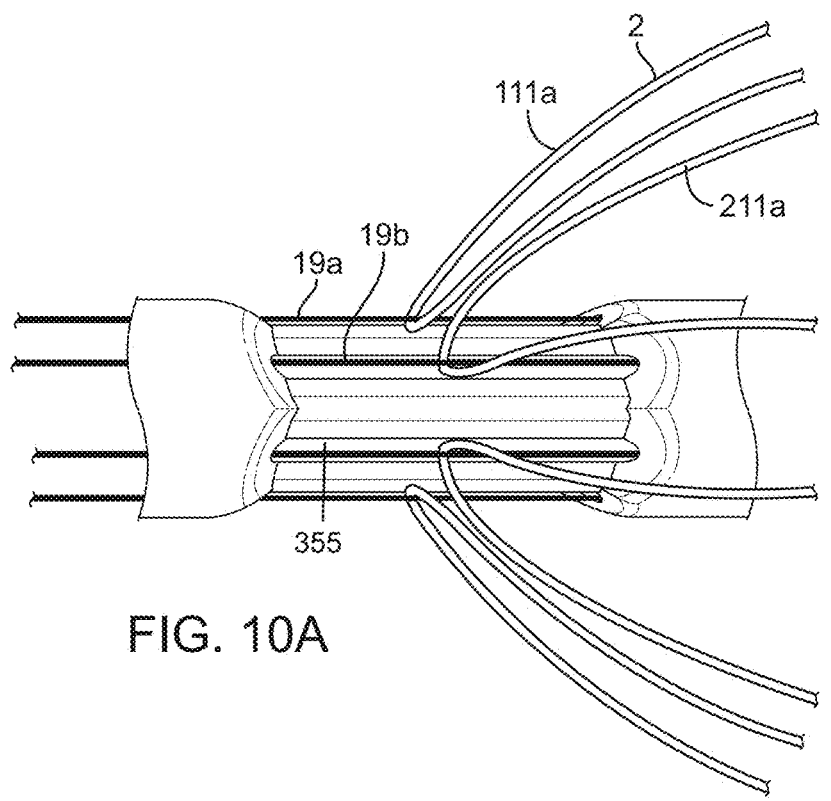
FIGS. 10A-10B show a mechanism for releasing the retention wires of a delivery device by pulling proximally on the retention wires.
Figure 12A:
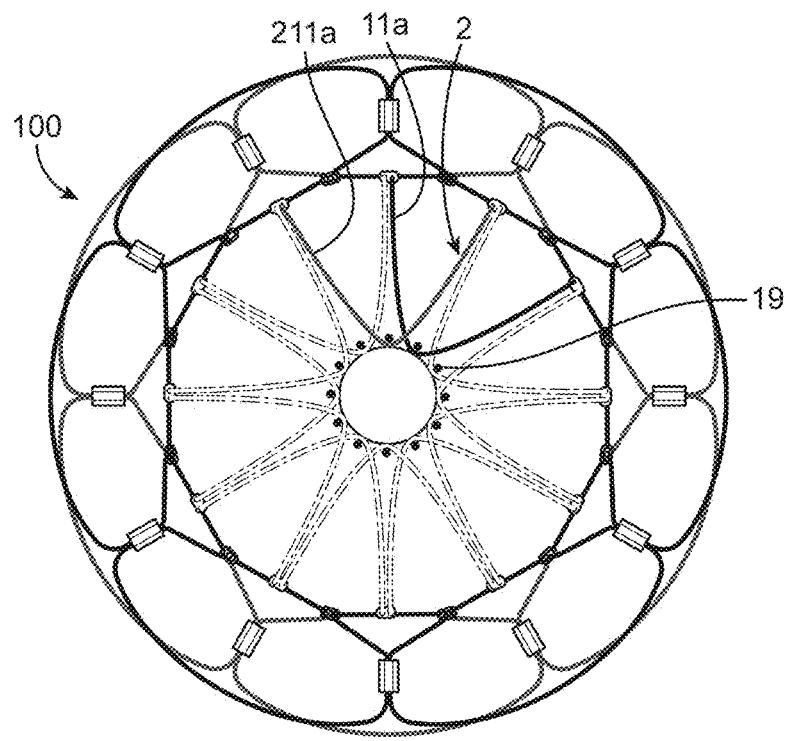
FIGS. 12A-12B show an exemplary mechanism for looping the proximal anchor with the retention wires of a delivery device.
Figure 12B:
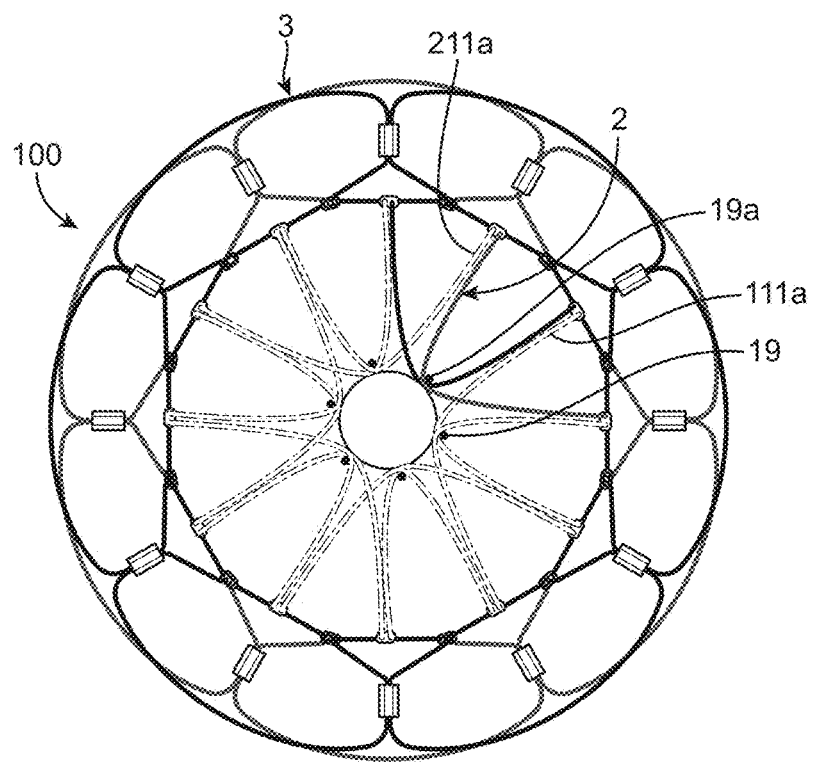

FIGS. 5B and 5C shows the prosthesis 100 partially deployed. That is, as the sheath 13 is pulled back with a lever 301 on the handle 300, the distal anchor 3 (previously collapsed into the sheath 11 with the peaks of the arcs extending distally) pops open. The proximal anchor 2, in turn, can remain connected to the delivery device 100 via the retention wires 19. That is, the retention wires 19 can pass through the multi-lumen central structure 17, through the arcs of the outer frame 122, 222 at apertures 355, and back into lumens of the structure 17. Referring to FIGS. 10A and 12A, in one embodiment, the proximal anchor 2 can be connected to the retention wires 19 such that neighboring arcs 111a, 211a of the proximal anchor 2 extend over neighboring retention wires 19a, 19b. In other embodiments (as shown in FIG. 12B), two neighboring arcs 111a, 211a can extend over a single retention wire 19a. Referring back to FIGS. 5B and 5C, as the retention wires 19 are pulled tight, the peaks of the arcs of the proximal anchor 2 will be pulled proximally, thereby causing the proximal anchor 2 to fold or cinch up to form a funnel shape at the proximal end of the distal anchor 3 (crimps 16, 26 of the proximal anchor 2 can be seen).

Figure 5D:
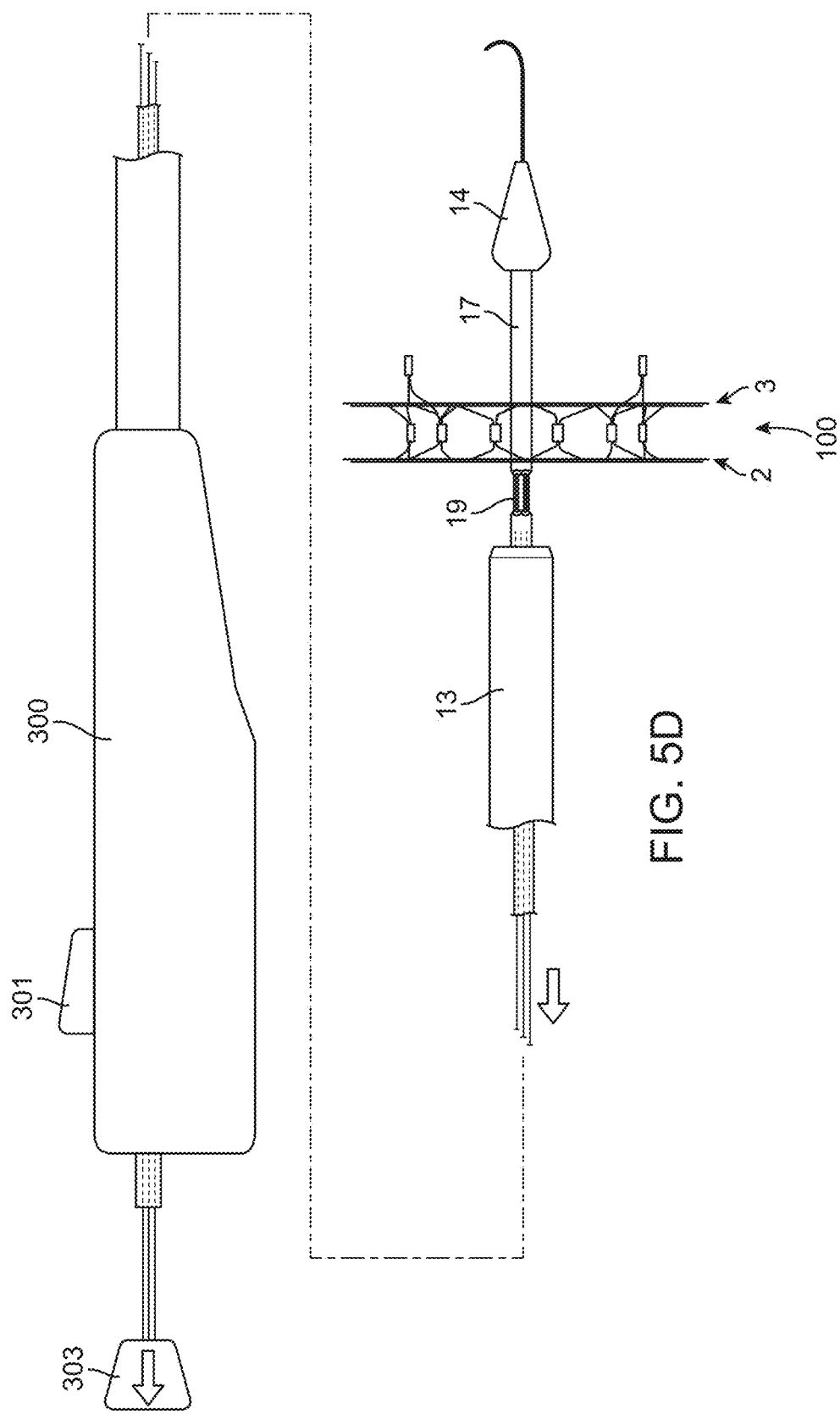
Figure 10B:
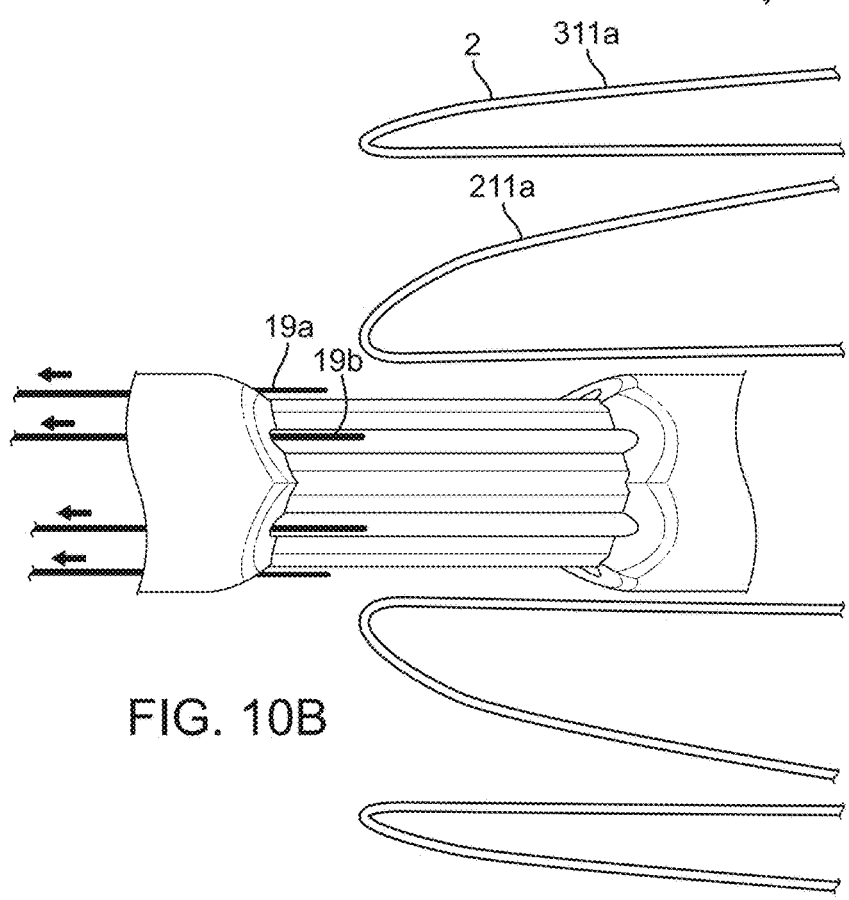
Figure 11A:
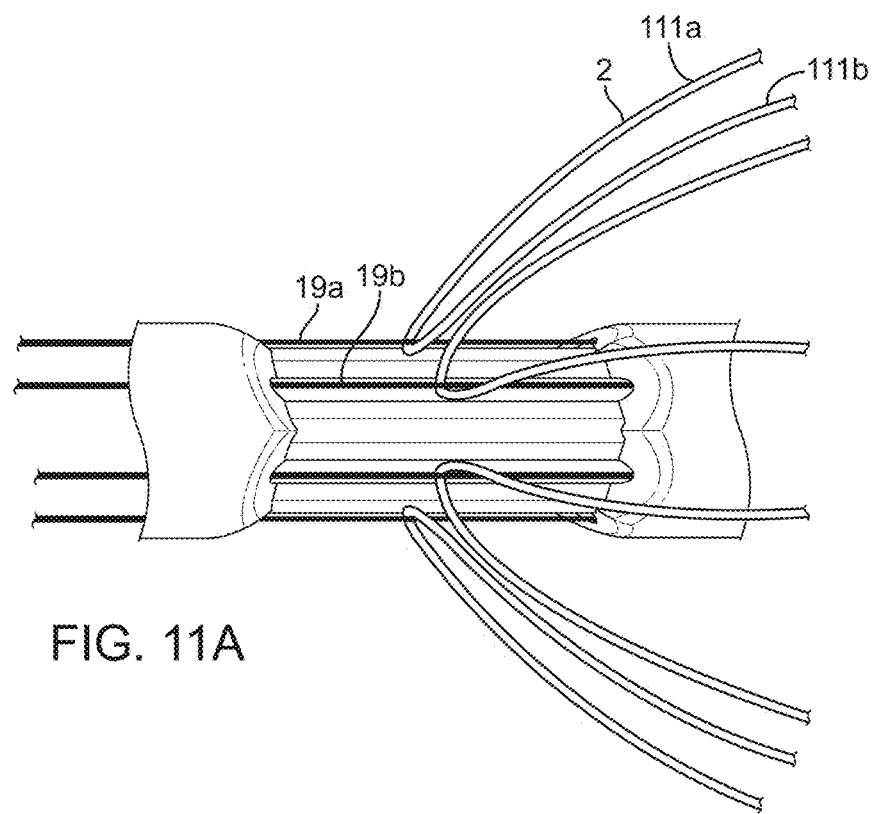
FIGS. 11A-11B show a mechanism for loosening the retention wires of a delivery device by pushing distally on the retention wires.
Figure 11B:
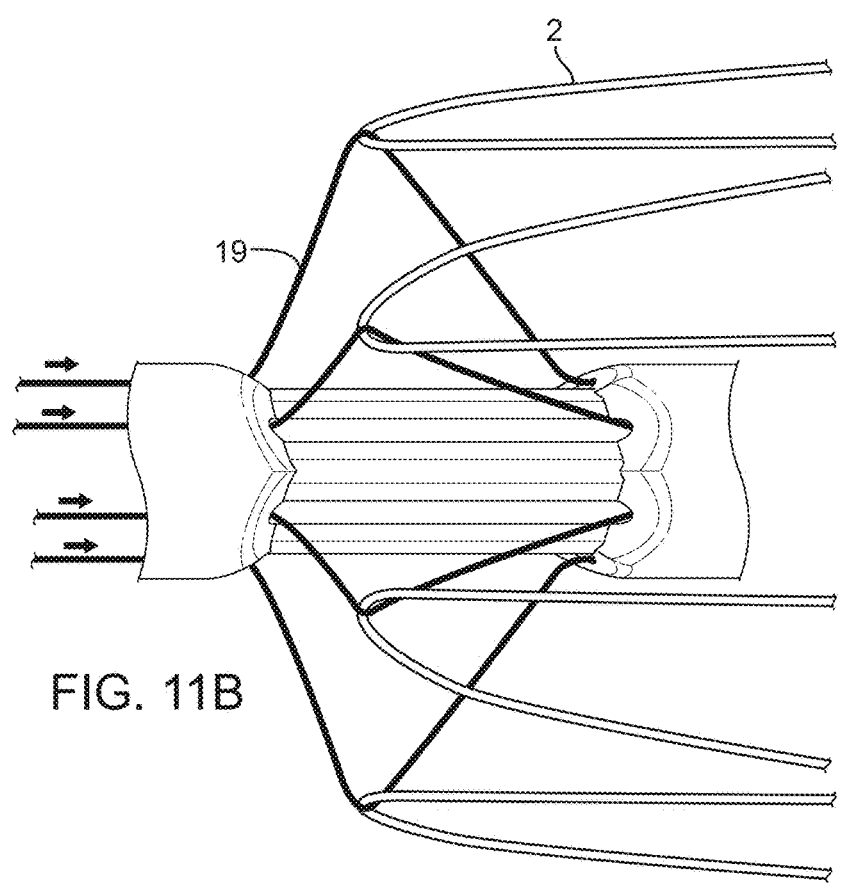

To expand the proximal anchor 2, the wires 19 can either be withdrawn or loosened (such as with a lever 303 on the handle), thereby allowing the proximal anchor 2 to self-expand into place, as shown in FIG. 5D. Referring to FIGS. 10A-10B, in some embodiments, the wires 19a can be withdrawn completely, thereby allowing the proximal anchor 2 to expand. In another embodiment, shown in FIGS. 11A-11B, the retention wires 19 can be formed of loops that, when loosened, i.e. pushed distally, allow the distal anchor 2 to expand without releasing the anchor 2. By using such a mechanism, the proximal anchor can be resheathed and moved (by retightening the retention members 19) if necessary. A mechanism on the handle can then be used to release the retention members 19 entirely.

Referring to FIG. 6A, to deploy the valve prosthesis 100 in a valve (such as the mitral valve), the guidewire 16 and delivery device 200 can be inserted through the native valve. Referring to FIG. 6B, as the outer sheath 13 of the device 200 is retracted relative to the central longitudinal structure 17, the distal anchor 3 of the valve prosthesis is exposed and self-expands (such as into the left ventricle). Once expanded, the distal anchor 3 may be retracted proximally against the distal-facing tissue of the cardiac chamber around the orifice, providing positive tactile feedback that the distal anchor 3 is oriented and positioned properly against the distal wall of the cardiac orifice. Further retraction of the sheath 13 exposes the central portion 4 of the valve prosthesis, allowing the central portion 4 to radially expand against the inner wall of the cardiac orifice.

Referring to FIG. 6C, to expand the prosthesis 100 on the other side of the cardiac orifice (i.e., in the left atrium), the central retention members 19 of the delivery device can be withdrawn or loosened as described above, thereby expanding the proximal anchor 2. The expanded proximal anchor 2 provides a second backstop to the valve prosthesis 100, allowing the prosthesis 100 to sandwich the valve orifice, such as the mitral valve orifice between the proximal and distal anchors 2, 3. As the device 100 expands, it foreshortens, moving the proximal anchor 2 and distal anchor 3 toward each other to provide a compressive force on tissue surrounding the cardiac orifice, such as the valve annulus.

Thus, in one example, as shown in FIG. 6D, the prosthesis can be delivered into the mitral valve orifice such that the distal anchor 3 sits within the left ventricle while the proximal anchor 2 sits within the left atrium. The struts 5 and leaflets 511 can extend distally into the left ventricle. Tissue of the mitral valve annulus can be captured between the anchors 2, 3. Further, the size of the prosthesis 100 can be such that the anchors 2, 3 extend within the chambers of the heart and much wider than the diameter of the orifice itself, thereby allowing for strong tissue capture and anchoring. In some embodiments, placement of the prosthesis can move the existing leaflets valves out of the way.

In some embodiments, as described above, the valve prosthesis 100 can be repositioned using the delivery device 200. That is, by pulling on the retention wires 19, the proximal anchor 2 can be cinched back down with the proximal arcs extending proximally. The distal anchor 3 can be collapsed into the sheath (with the arcs extending distally) either by pulling proximally on the prosthesis 100 or pushing the sheath 13 distally.

Figure 13:
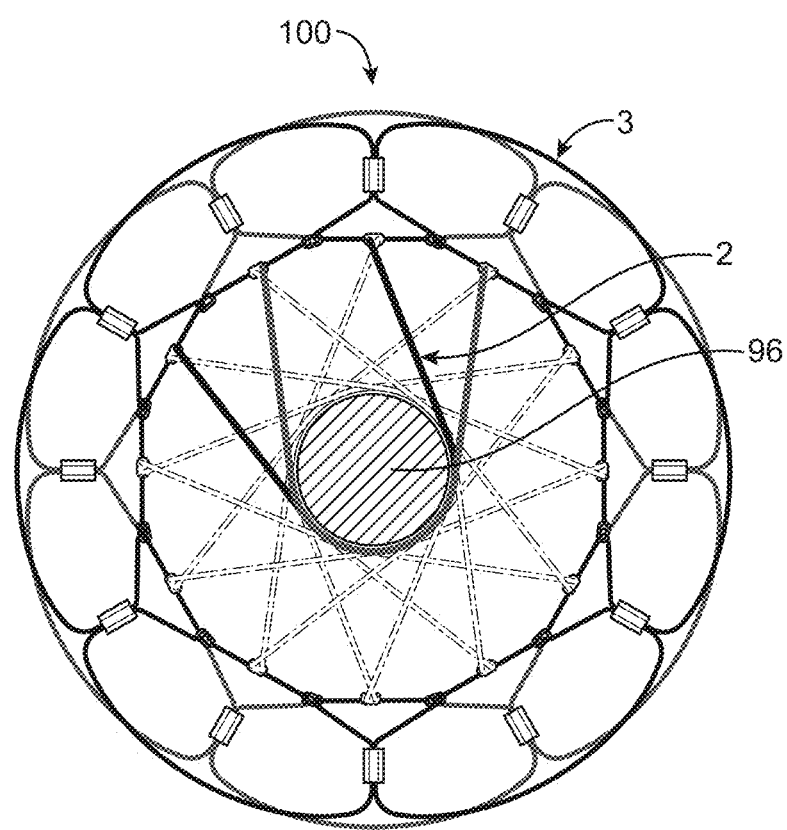
FIG. 13 shows an alternative mechanism for looping the proximal anchor over a delivery device.

Use of an alternative delivery device is shown in FIG. 13. As shown in FIG. 13, rather than including multiple retention wires, the delivery device can include a single elongate member 96 over which all of the arcs 111, 211 of the proximal anchor 2 are placed.

Figure 7:
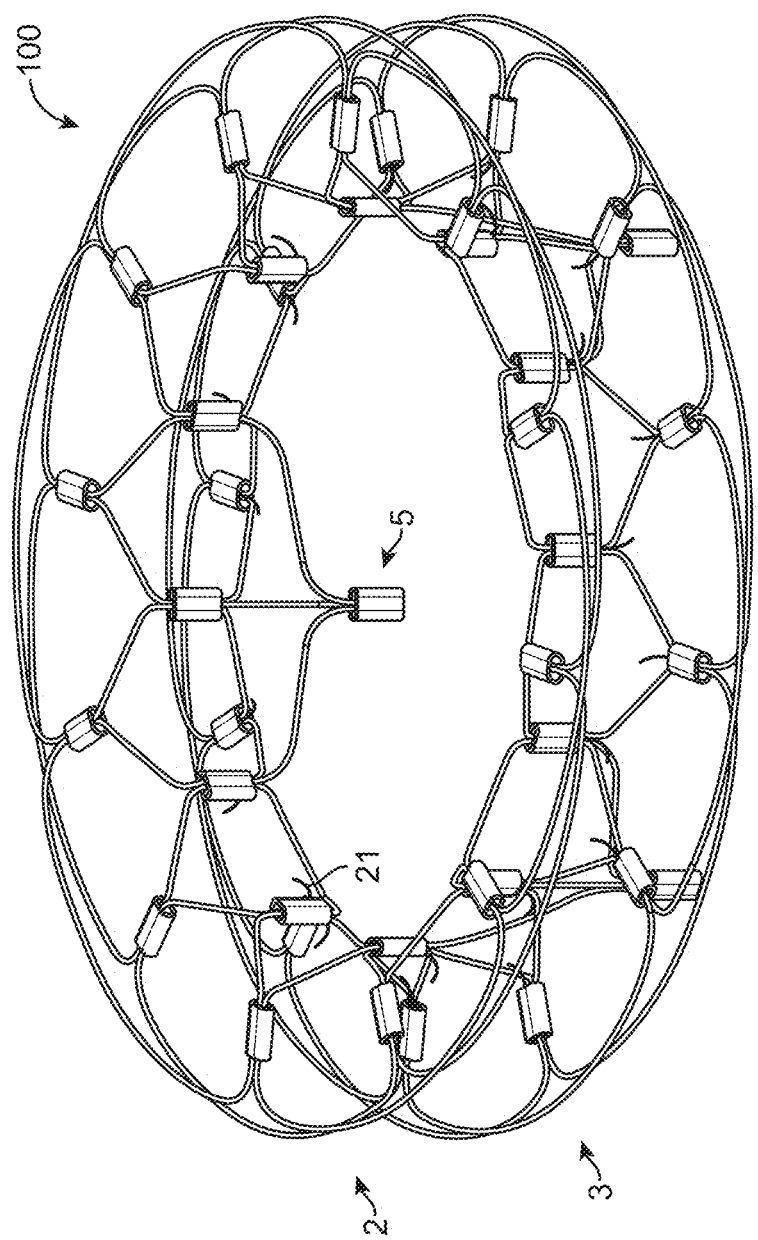
FIG. 7 shows a valve prosthesis structure with integral folding hooks for gripping cardiac tissue.
Figure 8B:
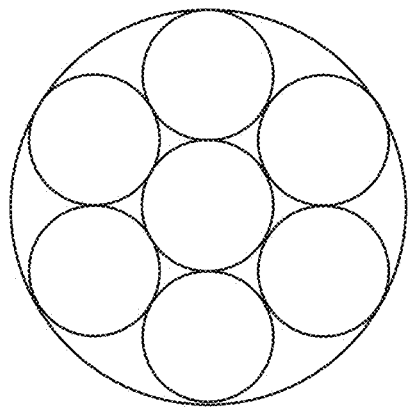
FIGS. 8A-9B show various wire rope configurations.
Figure 9B:
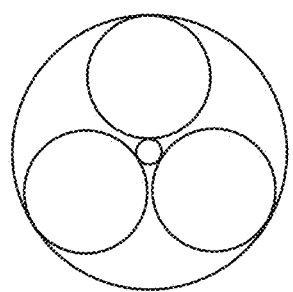
Figure 8A:
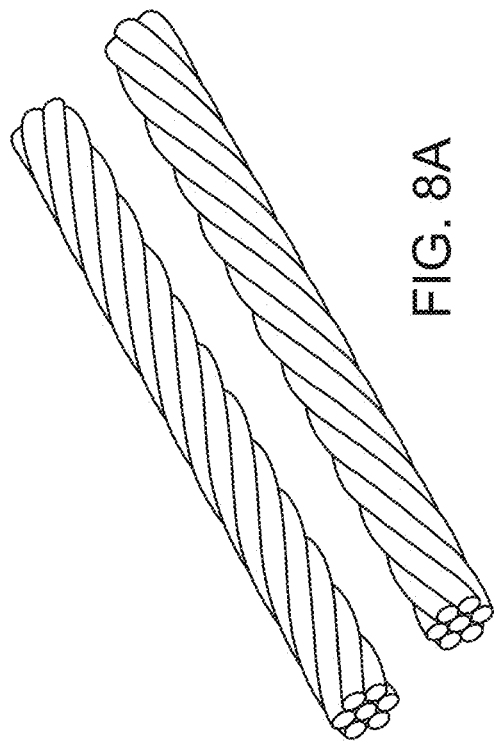
Figure 9A:
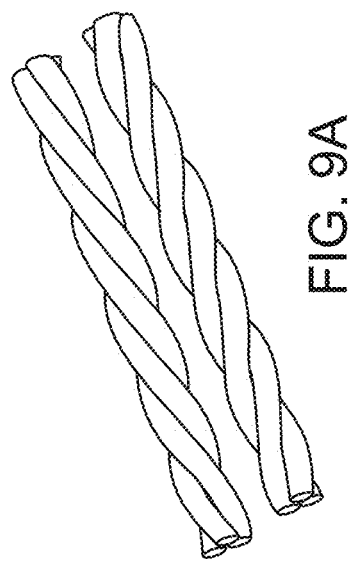

FIG. 7 shows an embodiment of the valve prosthesis 199 where retention hooks 21 are built into the device. The hooks 21 extend from toward the center of the device from the joints (e.g., crimps) of the distal anchor 3. The hooks may be made of nitinol and are curved so that as the distal anchor 3 is drawn toward the center longitudinal member 17 of the delivery device 200, the hooks flatten and collapse, allowing the outer sheath 13 of the delivery device 200 to slide smoothly over the hooks 21. As the outer sheath 13 is removed from the valve prosthesis 100 during delivery and the distal anchor 3 of the valve prosthesis opens, the hooks 21 expand into the tissue of the cardiac orifice. In some embodiments, the hooks 21 are only located on the distal anchor 3, as the distal anchor 3, when located on the ventricular side of the aorta, undergoes the highest pressure. In other embodiments, the hooks 21 are located on the proximal anchor 2 and/or the central portion 4.

In one embodiment, small hooks in the distal anchor 3 may be used to grip the valve leaflets. As the distal anchor 3 is retracted from the ventricle toward the mitral valve annulus, the hooks can pull the leaflets into a folded position just under the ventricular side of the mitral annulus.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A prosthetic mitral valve comprising:
   an expandable anchor comprising a first anchor, a central portion and a second anchor,
      wherein the first anchor comprises a first outer frame and a second outer frame,
      wherein, the first outer frame and the second outer frame expands radially outward from the central portion, the first outer frame comprising a plurality of first arcs joined together, and
      the second outer frame comprising a plurality of second arcs joined together,
   wherein the plurality of first arcs are approximately 90 degrees out of phase relative to the plurality of second arcs when the first anchor is viewed in an end view from the first anchor to the second anchor; and
   a plurality of replacement leaflets secured to the expandable anchor.

2. The prosthetic mitral valve of claim 1, wherein the first plurality of arcs are movable relative to the second plurality of arcs.

3. The prosthetic mitral valve of claim 1, wherein the first and second outer frames are substantially circular.

4. The prosthetic mitral valve of claim 1, wherein the proximal anchor and distal anchor are substantially parallel to one another.

5. The prosthetic mitral valve of claim 1, wherein the device is configured to foreshorten upon expansion of the proximal anchor, distal anchor, and central portion from the constrained configuration to the expanded configuration.

6. The prosthetic mitral valve of claim 1, wherein the proximal anchor and the distal anchor each have a diameter in the expanded configuration that is greater than a diameter of the central portion in the expanded configuration.

7. The prosthetic mitral valve of claim 1 wherein the second anchor comprises a plurality of arcs joined together.

8. A prosthetic mitral valve comprising:
   an expandable anchor comprising a first anchor, a central portion and a second anchor,
      wherein the first anchor comprises a first outer frame and a second outer frame,
      wherein, the first outer frame and the second outer frame expands radially outward from the central portion, the first outer frame comprising a plurality of first arcs joined together, and
      the second outer frame comprising a plurality of second arcs joined together,
   wherein the plurality of first arcs are approximately 90 degrees out of phase relative to the plurality of second arcs when the first anchor is viewed in an end view from the first anchor to the second anchor; and
   a plurality of replacement leaflets secured to the expandable anchor;
   wherein the device is configured to foreshorten upon expansion of the proximal anchor, distal anchor, and central portion from the constrained configuration to the expanded configuration.

9. The prosthetic mitral valve of claim 8, wherein the first plurality of arcs are movable relative to the second plurality of arcs.

10. The prosthetic mitral valve of claim 8, wherein the first and second outer frames are substantially circular.

11. The prosthetic mitral valve of claim 8, wherein the proximal anchor and distal anchor are substantially parallel to one another.

12. The prosthetic mitral valve of claim 8, wherein the proximal anchor and the distal anchor each have a diameter in the expanded configuration that is greater than a diameter of the central portion in the expanded configuration.

13. The prosthetic mitral valve of claim 8, wherein the second anchor comprises a plurality of arcs joined together.

* * * * *